United States Patent [19]

Shiratori et al.

[11] Patent Number: 5,348,888

[45] Date of Patent: Sep. 20, 1994

[54] DNA FRAGMENT CODING FOR MERCURIC REDUCTASE OF THIOBACILLUS, AND RECOMBINANT PLASMID

[75] Inventors: Toshikazu Shiratori, Chiba; Chihiro Inoue, Tokyo; Yoshichika Kitagawa; Tomonobu Kusano, both of Akita, all of Japan

[73] Assignee: Dowa Mining Co., Ltd., Tokyo, Japan

[21] Appl. No.: 133,347

[22] Filed: Oct. 8, 1993

Related U.S. Application Data

[63] Continuation-in-part of Ser. No. 966,610, Oct. 26, 1992, abandoned, which is a continuation of Ser. No. 396,900, Aug. 22, 1989, abandoned.

[30] Foreign Application Priority Data

Aug. 26, 1988 [JP] Japan ................................ 63-211984

[51] Int. Cl.$^5$ ........................ C12N 15/00; C12N 9/02
[52] U.S. Cl. ..................... 435/320.1; 536/23.2; 435/189; 435/172.1; 435/172.3
[58] Field of Search ..................... 435/191, 189, 320.1, 435/172.1, 172.3; 536/23.2

[56] References Cited

PUBLICATIONS

Shinatori et al. *J. Bact.*, Jun. 1989, vol. 171, No. 6, pp. 3458–3464.
Kusano et al. *J. Bact.*, May 1990, vol. 172, No. 5, pp. 2688–2692.
Olson et al., *J. Bact.*, Sep. 1982, vol. 151, No. 3, pp. 1230–1236.
Booth et al., *J. Gen. Microb.*, 1984, vol. 130, pp. 725–730.
Nishikawa et al., *Agric. Biol. Chem.*, vol. 49, No. 5, pp. 1513–1515.

*Primary Examiner*—Robert A. Wax
*Assistant Examiner*—Keith D. Hendricks
*Attorney, Agent, or Firm*—Nixon & Vanderhye

[57] ABSTRACT

Microorganisms of the genus Thiobacillus find utility in the mining industry in such applications as bacterial leaching, the treatment of mine drainage water and the deiron in hydrometallurgy process. This invention discloses a DNA fragment which codes for a mercuric reductase in microorganisms of the genus Thiobacillus and is useful in constructing a new strain of *Thiobacillus ferrooxidans* capable of fast growth. A recombinant plasmid incorporating the DNA fragment, a shuttle vector plasmid incorporating the DNA fragment, host cells and a method of transforming the host cells are also disclosed.

15 Claims, 15 Drawing Sheets

```
                                                                          HindIII                                        merC start
GTACGGGCAGTAAGTTGGGCCTACCCAACCCCTATAATAAGCTTATATCGTGATGACATAGCCGTGATGACCAGGAGGATCTGTCCATGTCA
                                                                                                                          M  S KpnI
GCCATAACCCGCATCATCGACAAAATTGGCATAGTCGGTACCATCGTCGGGTAGTTTCAGTTGCCGCCATGTGTTTCCCCGCAGCAGCGAGC
 A  I  T  R  I  I  D  K  I  G  I  V  G  T  I  V  G  S  F  S  C  A  M  C  F  P  A  A  A  S CTCGGCGCTGCAATCGGATTGGGCTTTCTCAGCCAGTGGGAAGGCCTGTTCGTGCAGTGGCTGATTCCGATTTTCGCCAGCGTGGCATTA
 L  G  A  I  G  L  G  F  L  S  Q  W  E  G  L  F  V  Q  W  L  I  P  I  F  A  S  V  A  L TTGGCGACCTTGGCGGGCTGGTTCTCGCACCGCCAATGGCAACGCCTGCTGGGCTCGATCGGTCCGGTGCTAGCGCTTGTCGGGGTG
 L  A  T  L  A  G  W  F  S  H  R  Q  W  Q  R  T  L  L  G  S  I  G  P  V  L  A  L  V  G  V
                     HpaI
TTTGGGTTAACGCATCACTTTCTGGACAAGGACCTGGCGCGTAATTTTTTATACCGGATTGGTGGTGATGTTCCTTGTCTCCATCTGG
 F  G  L  T  H  H  F  L  D  K  D  L  A  R  V  I  F  Y  T  G  L  V  V  M  F  L  V  S  I  W
                                                                                       merC end
GACATGGTCAATCCGGCAATCCGGGCTGGCGCGGACCGCTGCGGAACCGCGCTGAACTGGCGAAACGCCCGCTAGCTGAGCACATAGACACTTTGGAGGATAT
 D  M  V  N  P  A  N  R  C  A  T  D  G  C  E  T  P  A  P  R  S  *
merA start
TATGACCGAGAACGCGCCACCGAACTC
 M  T  E  N  A  P  T  E  L
```

Fig. 15

Comparison of the amino acid sequences of merC
Upper sequence: T. ferrooxidans strain E-15
Lower sequence: plasmid R100

```
         10        20        30        40        50
MSAITRIIDKIGIVGTIVGSFSCAMCFPAAASLGAAIGLGFLSQWEGLFV
*.****.**.*..*.****.**..*********************.****.
MGLMTRIADKTGALGSVVSAMGCAACFPALASFGAAIGLGFLSQYEGLFI 60        70        80        90       100
QWLIPIFASVALLATLAGWFSHRQWQRTLLGSIGPVLALVGVFGLTHHFL
*.**..*.**.*********** *.*** ***       **.*    *.*
SRLLPLFAALAFLANALGWFSHRQWLRSLLGMIGP----AIVFAATVWLL 100       120       130       140
DKDLARVIFYTGLVVMFLVSIWDMVNPAN-RCATDGCETPAPRS
. ..*.*. *****.*.**.*****.*..  .**** ** ** *
GNWWTANLMYVGLALMIGVSIWDFVSPAHRRCGPDGCELPAKRL
```

DNA FRAGMENT CODING FOR MERCURIC REDUCTASE OF THIOBACILLUS, AND RECOMBINANT PLASMID

This is a continuation in part application of U.S. Ser. No. 966,610 filed on Oct. 26, 1992, now abandoned which is a continuation application of U.S. Ser. No. 396,900 filed on Aug. 22, 1989, now abandoned.

FIELD OF THE INVENTION

The present invention relates to a DNA fragment coding for a mercuric reductase in microorganisms of the genus Thiobacillus, a recombinant plasmid incorporating said DNA fragment, a shuttle vector plasmid that incorporates said DNA fragment and that is capable of replication in either a microorganism of the genus Thiobacillus or the species *Escherichia coli*, host cells that can be transformed with this shuttle vector plasmid, and a method of transforming said host cells.

PRIOR ART

Microorganisms of the genus Thiobacillus occur frequently in areas around sulfide mineral ores and one of their uses is bacterial leaching of sulfide ores. Bacterial leaching is practiced very rarely in Japan on a commercial scale but is a routine technique in the United States of America, Canada, Australia, Chile and South Africa. In the United States of America, no less than 18–25% of the copper produced is reportedly recovered by bacterial leaching.

The use of microorganisms of the genus Thiobacillus is not limited to bacterial leaching. Utilizing their ability to oxidize ferrous ion ($Fe^{2+}$) to ferric ion ($Fe^{3+}$), commercial plants are operating in Japan at various sites to achieve such purposes as the treatment of mine drainage waters, deiron in hydrometallurgy process and the treatment of reducing gases such as $H_2S$. The cost of the treatment of mine drainage waters differs very greatly depending upon whether the iron ions in the drainage water is ferrous or ferric. The ferric ion is favorable from an economic viewpoint since calcium carbonate can be used as a neutralizing agent. Further, the treatment of drainage waters containing ferric ions results in a smaller formation of the precipitation product which is disposed of as waste. If microorganisms of the genus Thiobacillus are used in the deiron step of a hydrometallurgy process, the heating step can be eliminated and the amount of iron precipitate is sufficiently reduced to improve the precision of separation from other metallic ions. If those organisms are used in treatment of $H_2S$ gas, the necessary reaction can be carried out in a safe manner at ordinary temperatures and pressures, and at low cost [see "Application of Iron-Oxidizing Bacteria to Extractive Metallurgy" in Metallurgical Review of MMIJ, Vol. 3, No. 1, April (1986)].

While microorganisms of the genus Thiobacillus find utility in the mining industry as described above, a particularly useful species is *Thiobacillus ferrooxidans*. This is an autotrophic bacterium and grows much more slowly than heterotrophic and aerobic bacteria. Therefore, bacterial leaching using this organism requires a very large field, as well as a large reactor for drainage water treatment. The doubling time of *E. coli* is about 20 minutes whereas that of *Thiobacillus ferrooxidans* is as long as about 10 hours. Combining these figures with the fact that the yields of *E. coli* and *T. ferrooxidans* cells in a 1 l medium are about 6 g and 0.1 g, respectively, one could imagine how great the size required for the leaching operation and the reactor would be. Since the production costs of the leaching facilities and equipment and the cost of treatment depend largely upon these factors, the use of *T. ferrooxidans* has been quite limited in spite of its utility.

With a view to finding organisms of the genus Thiobacillus capable of fast growth, random screening was performed as in the case of using other organisms, but no great success has been achieved. Under these circumstances, it is desired to construct a new strain of *T. ferrooxidans* by gene manipulation but to this end, a vector carrying all appropriate marker for the selection of a useful strain is necessary.

In connection with this, a cloning vector has already been known and disclosed by Rawlings et al. in Japanese Patent Public Disclosure No. 60-91988 entitled "Process For Preparing Selectable Shuttle Cloning Vectors for *Thiobacillus ferrooxidans*" and in Japanese Patent Public Disclosure No. 60-102189 entitled "Method of Constructing Arsenic Resistant Vectors" The vectors disclosed Japanese Patent Public Disclosure No. 60-91988 contain a pBR325-derived chloramphenicol resistance gene as a marker gene. However, *Thiobacillus ferrooxidans* grows at a pH in the neighborhood of 2 and it is known that chloramphenicol and other antibiotics that are commonly employed in gene manipulation for selecting drug resistant transformants are labile under such strong acidic conditions [Phyllis, A. W. Martin et al. Eur. J. Appl. Microbiol. Biotechnol., Vol. 18, pp. 392–394 (1983) and P. Vista et al., "Fundamental and Applied Biohydrometallurgy", ELSEVIER, pp 429–442].

Further, organisms of the genus Thiobacillus are obligate autotrophic bacteria and their growth is inhibited by many organic substances. Therefore, there is a high likelihood that the growth of Thiobacillus is inhibited by the presence of antibiotics or their decomposition products in media. According to Rawlings et al., the arsenic used as an inhibitor factor in the invention described in Japanese Patent Public Disclosure No. 60-102189 is present as $As_2O_3$ or $AsO_4^{3-}$ in a medium for *T. ferrooxidans* and their minimum inhibitory concentrations (MIC) are 16 $\mu$M and 32 mM, respectively. In the medium, $As_2O_3$ is gradually oxidized to $AsO_4^{3-}$, with the corresponding decrease in its inhibitory action on the organism. Even if arsenic is added as $AsO_4^{3-}$ to the medium in a sufficient amount to inhibit cell growth, it reacts with $Fe^{3+}$ that forms as a result oxidation of ferrous ions by *T. ferrooxidans*, whereupon precipitates as $FeAsO_4$ and is no longer capable of working as an inhibitor factor.

Under these circumstances, the present inventors conducted intensive studies in order to establish a vector harboring a marker gene useful in gene manipulation of *Thiobacillus ferrooxidans* and reached the conclusion that resistance to mercury ion was effective as a selection marker. Based on this conclusion, they filed a patent application on an invention entitled "Recombinant Plasmid for Organisms of the Genus Thiobacillus, Mercury Resistant Vector Plasmid, and Methods of Constructing Them" on Feb. 27, 1987 (Japanese Patent Application No. 62-44773). The vector disclosed in Japanese Patent Application No. 62-44773 has a mercury resistance gene cut out from the Pseudomonas derived plasmid pME285 (Tn501 $mer^R$). When this vector was used in transforming *T. ferrooxidans*, both the efficiency of transformation and the yield of expression were so low that a further improvement seemed necessary before the vector could be used in practical applications. One the reasons for the poor performance of the vector would be that the E. coli promoter is not fully active in the cells of T. ferrooxidans.

The chloramphenicol resistance gene and the arsenic resistance gene used as marker genes in the vectors described in Rawlings et al. Japanese Patent Application Nos. 60-91988 and 60-102189, respectively, are derived from heterotrophlc bacteria. The expressions of these genes in E. coli was established but no confirmation has been made that they are also expressed in T. ferrooxidans. According to another study conducted by Rawlings et al., when plasmid pDER502 capable of expressing in E. coli was introduced into T. ferrooxidans, it was not expressed at all or was expressed only with low efficiency [M. E. C. Barrow, D. E. Rawlings and D. R. Woods, "Production and Regeneration of Thiobacillus ferrooxidans Spheroplasts" in Applied and Environmental Microbiology, Vol. 50, No. 3, pp. 721–723 (1985)].

Unlike with E. coli, a gene cannot be introduced into the cells of Thiobacillus by treatment with $CaCl_2$. Instead, attempts have been made to introduce a gene by first changing the cells of Thiobacillus into spherical forms (spheroplasts) and then treating them with polyethylene glycol. A problem with this technique is that the spheroplasts must be restored to their original cell shape by synthesizing the cell wall under suitable conditions. In the case of Thiobacillus, if the spheroplasts into which a gene of interest has been introduced are placed at a pH of 2 which is optimal for their growth, the cells are incapable of replicating the cell wall at that pH, with a subsequent significant decrease in the number of viable cells. A need has therefore been recognized for the development of an effective method for introducing a DNA of interest into cells if gene manipulation is to be performed on T. ferrooxidans.

SUMMARY OF THE INVENTION

An object, therefore, of the present invention is to provide a DNA fragment coding for a mercuric reductase derived from Thiobacillus ferrooxidans and which is an effective selection marker gene for organisms of the genus Thiobacillus.

Another object of the present invention is to provide a 4.8 kb SalI-SalI DNA fragment isolated from genomic DNA of a Thiobacillus ferrooxidans mercury resistant strain, or a shorter fragment thereof having a size at least 2.3 kb and containing a 2.1 kb segment which extends between two HindIII sites, wherein said DNA fragment contains the 56 kDa mercuric reductase gene (merA) and the 16 kDa protein gene (merC), said DNA fragment is capable of hybridizing with the mercuric resistance gene of Pseudomonas transposen Tn501, and said DNA fragment is capable of providing mercury resistance with Escherichia cell cells when said cells are transformed with E. coli plasmid carrying said DNA fragment.

A further object of the present invention is to provide an isolated DNA fragment which contains a 56 kDa mercuric reductase gene (merA) and a 16 kDa protein gene (merC), which DNA fragment is capable of providing mercury resistance with mercury susceptible Thiobacillus ferrooxidans cells when said cells are transformed with a plasmid carrying said DNA fragment and a replication origin of T. ferrooxidans.

BRIEF DESCRIPTION OF THE DRAWINGS

FIG. 1 is an autoradiogram showing the results of dot hybridization of T. ferrooxidans using transposen Tn501 derived mercury resistance gene as a probe.

FIG. 14 shows the nucleotide sequence of the gene encoding the 16 kDa protein as well as the deduced amino acid sequence; and FIG. 15 compares the deduced amino acid sequence from FIG. 14 and that of merC gene from plasmid R100.

DETAILED DESCRIPTION OF THE INVENTION

Figure 2:
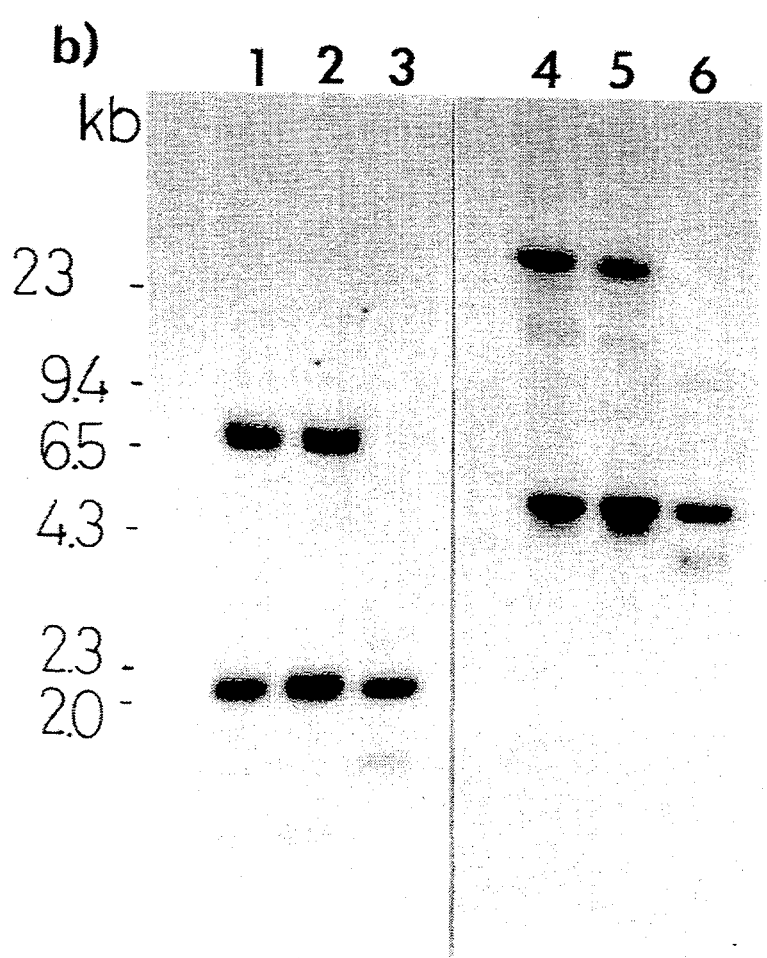
FIG. 2 is an autoradiogram showing the results of Southern hybridization of T. ferrooxidans using transposon Tn501 derived mercury resistance gene as a probe.

Thiobacillus ferrooxidans is resistant to many heavy metals but it is usually sensitive to uranium, silver and mercury ions. Some strains of T. ferrooxidans, however, are known to have resistance to mercury ion. Their resistance to mercury ion is exhibited either on account of the presence of a mercuric reductase or possibly by the blocking of the transport of mercury ions through the cell wall. As a matter of fact, the presence of a mercuric reductase has been detected in mercury-resistant strains of T. ferrooxidans [Jayne B. Robinson, Olli H. Tuovinen, "Mechanism of Microbial Resistance and Detoxification of Mercury and Organomercury Compounds: Physiological, Biochemical and Genetic Analysis" in Microbiological Reviews, Vol. 48, No. 2, pp. 95–124 (1984)].

Mercury ion resistance systems have been discovered both from Gram-negative and Gram-positive bacteria. They are chiefly encoded in plasmids or transposons but sometimes in chromosomes as in the case of *Staphylococcus aureus* and some marine bacilli. Mercury ion resistance system are known to assume an operon structure in plasmid R100 and transposon Tn501 both of which have a mercury resistance gene and have been the subject of extensive studies. The first gene of the Tn501 mer operon is a regulatory gene merR and its gene product is an operator binding protein. Downstream of the merR gene are located an operator-promoter region, which are followed by four consecutive genes, merT, merP, merA and merD. In the R100 met operon, merC is situated in the region between merP and merA.

The protein produced by merT takes part in the migration of $Hg^{2+}$ ions across the cell membrane. The product of merP is a periplasmic mercury binding protein. The product of merA is a mercuric reductase protein that volatilizes mercury. The functions of the products of merC and merD in the R100 mer operon have not yet been fully clarified but presumably merC would supplement merA.

The 4.8 kb SalI-SalI fragment of the invention may be obtained by various methods. A convenient method is to subject genomic DNA from *T. ferrooxidans* strain E-15 (deposited with the Fermentation Research Institute, the Agency of Science and Technology on Aug. 22, 1988 under Accession Number FERM BP-10217) to SalI digestion. The SalI Fragments are linked to the linker cloning SalI site of *E. coli* plasmid pUC18 to prepare hybrid DNAs. *E. coli* DH5α is transformed with the resulting hybrid DNAs. The transformed cells of *E. coli* DH5α are cultivated on a solid medium in a plate. Colonies having the DNAs inserted at the linker cloning site of pUC18 can be selected with pigment production by the colonies. Then, colony hybridization is performed with the $mer^R$ portion of plasmid pME285, coding for the mercury resistance gene, derived from Pseudomonas PAO 25 [Ito et al., Gene, 36, pp.27–36 (1985)] being used as a probe. Colonies which hybridize with the probe will contain the 4.8 kb SalI-SalI fragment of the invention.

Examples of plasmids containing the 4.8 kb SalI-SalI fragment are plasmids pTM314 and pTM315, construction of which will be described in more detail in examples hereinafter. The fact that the former contains the 4.8 kb SalI-SalI fragment will be stated in Example 9 B.

Figure 7:
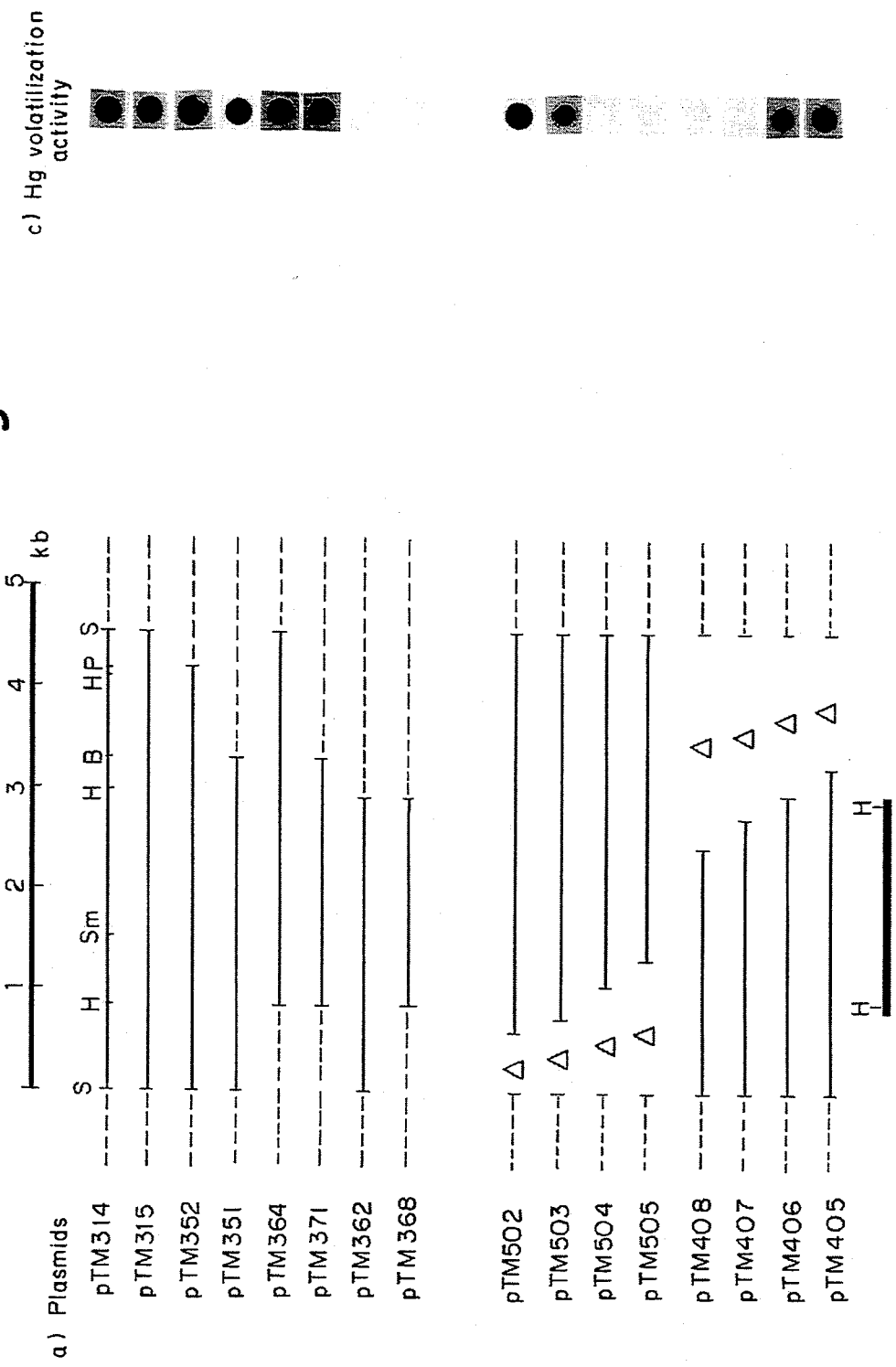
FIG. 7 includes physical maps of pTM314 and deletion plasmids thereof, and pictures showing their mercury volatilizing activity.

The restriction map of pTM314 is shown at the top of FIG. 7. FIG. 7 shows the strategy used in identifying that the 56 kDa mercuric reductase gene (merA) and the 16 kDa protein gene (merC) are contained in the region of a size at least 2.3 kb and containing a 2.1 kb segment which extends between the two HindIII sites. It will be easy for a skilled person to prepare a shorter fragment containing the region of a size at least 2.3 kb and containing a 2.1 kb segment which extends between the two HindIII sites.

The 4.8 kb SalI-SalI fragment or a shorter fragment thereof of the invention is capable of providing mercury resistance with *E. coli* cells when said cells are transformed with an *E. coli* plasmid carrying said DNA fragment. Examples of such *E. coli* plasmids include pBR322, pUC118, pUC119, and etc. Such plasmids should contain a replication origin which is capable of functioning in *E. coli* cells. Insertion of the fragment into an *E. coli* plasmids may be effected by any conventional means; for example, the plasmid may be cleaved with SalI and then the SalI-SalI fragment may be ligated. Expression of the ligated genes may also be effected by any conventional means.

The 4.8 kb SalI-SalI fragment or a shorter fragment thereof of the invention is capable of providing mercury resistance with *T. Ferrooxidans* which is not mercury resistant. For this purpose, the SalI-SalI fragment or a shorter fragment thereof may be ligated to an *E. coli* plasmid containing a replication origin which is capable of functioning in *T. Ferrooxidans* cells. A replication origin capable of functioning in *T. Ferrooxidans* cells may be derived from, for example, plasmids pTSY91, pTSB121 and pTNA33 which are contained in *T. ferrooxidans* strains Y5-9 (FERM BP-9157), B-12 (FERM BP-9156) and MA3-3 (FERM BP-10965), respectively. These plasmids may be cleaved with either PstI or EcoRV and ligated to an *E. coli* plasmid such as pBR322 or pUC18 which has been cleaved with EcoRV or PstI, respectively to provide a replication origin of *T. Ferrooxidans* with the *E. coli* plasmid. Insertion and expression of the 4.8 kb SalI-SalI fragment or a shorter fragment thereof of the invention may be effected in the same way as described above.

The present invention will be described in more detail hereinunder.

The present inventors accomplished the present invention by the following process:

(1) screening for a *T. ferrooxidans* strain having a mercuric reductase;

(2) establishing the location of a gene coding for a *T. ferrooxidans* mercuric reductase (hereinafter referred to simply as a mercuric reductase gene)—it was found be located on genome;

(3) extracting and purifying the genomic DNA of *T. ferrooxidans;*

(4) cloning the purified DNA fragment into an *E. coli* plasmid;

(5) selecting for the *E. coli* colonies transformed with the cloned *E. coli* plasmid;

(6) extracting a plasmid DNA from the selected *E. coil* colonies and cutting out the mercuric reductase gene portion of the plasmid;

(7) determining the nucleotide sequence of the DNA fragment obtained in step (6), as well as the amino acid sequence of the mercuric reductase encoded by said fragment; and (8) constructing a shuttle vector plasmid by linking the *T. ferrooxidans* derived mercuric reductase gene obtained in step (6) with *T. ferrooxidans* and *E. coli* plasmids containing their respective replication origins.

The screening in step (1) was conducted in the following manner. First, ten strains of *T. ferrooxidans* (B-12, B-19, E-6, E-7, E-9, E-15, E-24, M4-6, U4-25 and Y5-9) were isolated from various mining sites in Japan, and MIC measurements were conducted for $HgCl_2$ in order to evaluate the mercury resistance of these strains. The results are shown in Table 1, on the basis of which the following five strains were selected as mercury resistant strains: E-6, E-7, E-15, E-24 and U4-25.

TABLE 1

| MIC of $HgCl_2$ in *T. ferrooxidans* | | | | | | | | | |
|---|---|---|---|---|---|---|---|---|---|
| Strains | | | | | | | | | |
| B-12 | B-19 | E-6 | E-7 | E-9 | E-15 | E-24 | M4-6 | U4-25 | Y5-9 |

TABLE 1-continued

| HgCl$_2$ (μg/ml) | 0.2 | 0.2 | 1.0 | 0.75 | 0.3 | 0.75 | 1.5 | 0.2 | 1.0 | 0.2 |
|---|---|---|---|---|---|---|---|---|---|---|

In the next step, in order to select for strains that exhibited mercury resistance on account of the presence of a mercury reducing enzyme, a test was conducted to examine the mercury-dependent oxidation of NADPH by the extracts of strains E-6, E-7, E-15, E-24 and U4-25. The results are shown in Table 2. The test measures the mercury ion reducing activity of the strains by utilizing the fact that when mercury is reduced to metallic form, NADPH is oxidized to NADP in a mercury-dependent manner.

TABLE 2

Mercury-dependent oxidation of NADPH by the extracts of *T. ferrooxidans*

| | \multicolumn{10}{c}{Strains} |
|---|---|---|---|---|---|---|---|---|---|---|
| | B-12 | B-19 | E-6 | E-7 | E-9 | E-15 | E-24 | M4-6 | U4-25 | Y5-9 |
| Δ340 nm/ 20 min[a] | —[b] | — | 0.97 | 1.35 | — | 1.02 | 0.12 | — | 0.07 | — |

[a]Values of Δ340 nm/20 min were determined by the following formula: (Initial absorbance at 340 nm) - (Absorbance at 340 nm after incubation at 37° C. for 20 min).
[b]Not tested.

The above data shows that strains E-6, E-7 and E-15 have both mercury resistance and the ability to volatalize mercury.

Figure 1:
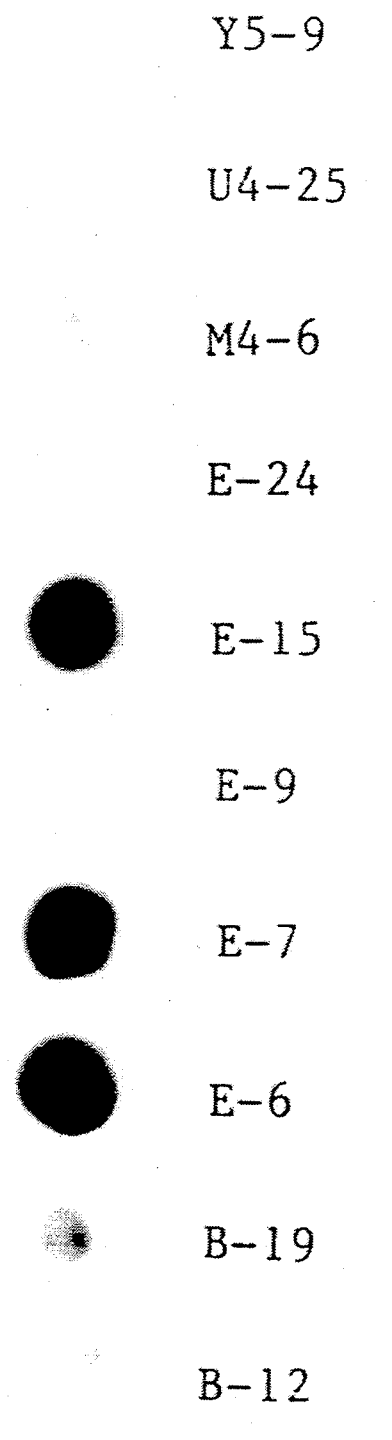

In the next step, the location of a mercuric reductase gene in the ten strains of *T. ferrooxidans* under test was determined by dot hybridization using as a probe a DNA fragment (mer$^R$) coding for the mercury resistance gene in plasmid pME285 derived from Pseudomonas PAO 25 [Ito et al., Gene, 36, pp. 27-36 (1985)]. The mercuric reductase gene of interest was found to occur genomically in three *T. ferrooxidans* strains, E-6, E-7 and E-15 (see FIG. 1). These strains were isolated from the iron oxidizing step involving the use of iron oxidizing bacteria at a hydrometallurgtcal processing workshop, Kosaka Refinery, Dowa Mining Co., Ltd.

The fragment of the genomic DNA in each of the three strains that was cleaved with restriction enzymes HindIII and EcoRI and the SalI fragment were subjected to Southern hybridization with the mer$^R$ portion of pME285 being used as a probe (FIG. 2). Since the genomic DNAs of the three strains hybridized with the probe at different positions, the respective strains were found to harbor different mercuric reductase genes.

A SalI fragment of genomic DNA in strain E-15 (deposited with the Fermentation Research Institute, the Agency of Science and Technology on Aug. 22, 1988 under Accession Number FERM BP-10217) was linked to the linker cloning SalI site of *E. coli* plasmid pUC18 to prepare a hybrid DNA. *E. coli* DH5α was transformed with the resulting hybrid DNA. The transformed cells of *E. coli* DH5α were cultivated on a plate medium. From the about 2,000 colonies obtained, 500 colonies having the difference DNA fragment inserted at the linker cloning site of pUC18 were first selected with pigment production by colony being used as a criterion. Then, colony hybridization was performed with the mer$^R$ portion of pME285 being used as a probe, so as to select two *E. coli* colonies containing pUC18 that had the SalI fragment of genomic DNA inserted therein. These two plasmids were novel and named pTM314 and pTM315.

Physical maps of these plasmids were prepared using various restriction enzymes (FIGS. 4 and 5) and the restriction enzyme digested fragments were subjected to electrophoresis. The physical maps and the electrophoretic patterns obtained showed that the SalI fragment of genomic DNA in *T. ferrooxidans* strain E-15 was oriented in pTM314 and pTM315 in entirely opposite directions.

The mercury resistance of *E. coli* strain DH5α transformed with these plasmids was at least 10 times as high as the sensitive strain into which the mercuric reductase gene was not introduced. This shows that the *T. ferrooxidans* mercuric reductase gene in the transformed cells of *E. coli* utilized its own promoter to be expressed in the transformants.

Deletion analysis of pTM314 and pTM315 (see Examples 6 and 7 to be provided hereinafter) and the physical map prepared for the inserted SalI fragment (FIG. 8) showed that a 2.3-kb region spanning the 2.1-kb HindIII fragment took part in the expression of mercury resistance.

Figure 9:
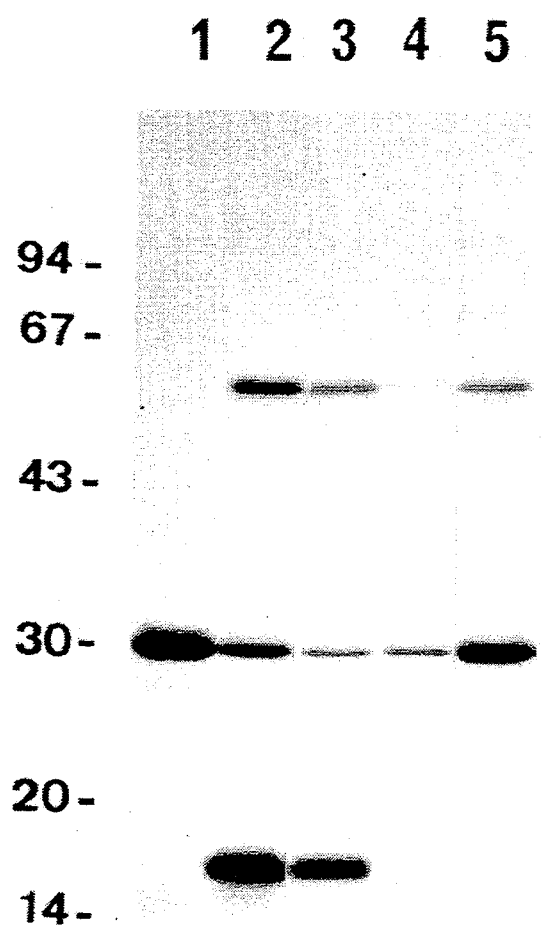
FIG. 9 is a picture showing the electrophoretic pattern of a T. ferrooxidans derived mercuric reductase.

The proteins produced by the plasmids were analyzed by the maxicell method and it was found that the 2.3-kb region encoded two kinds of polypeptide having molecular weights of 56 kDa and 16 kDa (FIG. 9). Since the merA gene products of R100 and Tn501 had respective molecular weights of 58,905 and 58,727 daltons, the 56 kDa protein was assumed to be a mercuric reductase (merA gene product).

The nucleotide sequence of the genomic DNA in the region coding for the mercuric reductase of *T. ferrooxidans* was determined by the dideoxynucleotide chain-termination procedure. Also determined was the amino acid sequence of the mercuric reductase. The determined nucleotide sequence of the genomic DNA and the amino acid sequence of the reductase are shown in the following Tables 3 and 4. respectively.

TABLE 3

Nucleotide Sequence

```
  1         10         20         30         40         50
ATGACCGAGAACGCGCCCACCGAACTCGCTATCACTGGCATGACCTGCGA 60         70         80         90        100
CGGTTGCGCCGCGCATGTGCGCAAAGCACTCGAAGGCGTGCCCGGCGTAC 110        120        130        140        150
GCGAGGCGCAGGTGTCCTACCCGGATGCCACGGCCCGGGTCGTGCTGGAG
```

TABLE 3-continued

Nucleotide Sequence

```
          160       170       180       190       200
GGCGAGGTGCCGATGCAGCGGCTAATCAAGGCGGTGGTTGCAAGTGGCTA 210       220       230       240       250
TGGTGTGCATCCACGGAGCGACGGTGCCTCCTCCACAAACGATGGACAGG 260       270       280       290       300
AGCTACACATCGCTGTGATCGGCACCGGCGGAGCGGCGATGGCGTGCGCA 310       320       330       340       350
TTGAAGGCTGTCGAGCGGGGCGCGCGCGTGACGCTGATCGAACGCAGCAC 360       370       380       390       400
CATCGGCGGCACCTGCGTGAACATCGGTTGCGTGCCGTCCAAGATCATGA 410       420       430       440       450
TCCGCGCCGCCCATATCGCCCACCTCCGCCGGGAAAGCCCATTCGATGGC 460       470       480       490       500
GGCATCCAGGCGGTCGCGCCGACCATCCAGCGCACAGCGCTGCTGGTCCA 510       520       530       540       550
ACAGCAGGCCCGTGTCGATGAACTGCGTCACGCCAAGTACGAAGGCATCC 560       570       580       590       600
TGGACGGCAACCCGGCCATCACCGTTCTGCGCGGTGAAGCGCGTTTCAAG 610       620       630       640       650
GACAGCCGGAGTGTTGTCGTCCATTTGAACGATGGTGGCGAGCGCGTCGT 660       670       680       690       700
AATGTTCGACCGCTGCCTGGTTGCCACGGGCGCCAGTCCGGCCGTGCCGC 710       720       730       740       750
CGATTCCCGGCTTGAAAGACACTCCTTATTGGACCTCCACCGAAGGGCTG 760       770       780       790       800
GTCAGCGAATCGATCCCCGAGCGTCTGGCCGTGATCGGCTCGTCGGTGGT 810       820       830       840       850
GGCGCTGGAACTGGCGCAAGCCTTCGCCCGGCTCGGCAGCCATGTGACGA 860       870       880       890       900
TCCTGGCGCGCGGCACCTTGTTCCTCCGGGAAGACCCGGCCATCGGTGAG 910       920       930       940       950
GCCATCACGGCGGCGTTTCGCGCCGAAGGCATCGAGGTGCTGGAGCACAC 960       970       980       990       1000
CCAGGCCAGCCAGGTCGCTTATGCGGATGGCGAATTTGTGCTAGCCACCG 1010      1020      1030      1040      1050
GGCACGGCGAACTGCGCGCCGATAAGCTGCTGGTCGCCACTGGTCGCGCA 1060      1070      1080      1090      1100
CCGAACACACGCCGCCTGAATCTGGAAGCGGCGGGCGTGGCCATCAATGC 1110      1120      1130      1140      1150
GCAAGGGGCCATCGTCATCGACCAGGGTATGCGCACGAACAGCCCGAACA 1160      1170      1180      1190      1300
TTTACGCCGCTGGCGACTGCACCGACCAGCCGCAATTCGTCTACGTGGCG 1210      1220      1230      1240      1250
GCAGCGGCCGGCACCCGTGCGGCCATCAACATGATGGGCGGTAGTGCAGC 1260      1270      1280      1290      1300
CCTGGACTTGACGGCGATGCCAGCCGTGGTGTTCACCGATCCGCAAGTGG 1310      1320      1330      1340      1350
CGACTGTGGGTTACAGCGCGGAAGCGCATCGCGACGGCATCGAAACCGAC 1360      1370      1380      1390      1400
AGCCGCATGACGCTCGACAACGTGCCGCGGGCGCTCGCCAATTTCAATAC 1410      1420      1430      1440      1450
ACGCGGCTTCATCAAGCTGGTAGCCGAAGTGGGCAGTGGCTCGCTAATCG
```

TABLE 3-continued

Nucleotide Sequence

```
          1460       1470       1480       1490       1500
      GCGTGCAGGTGGTCGCCCCGGAAGCGGGCGAGCTGATCCAGACTGCCGCG 1510       1520       1530       1540       1550
      CTGGCGATTCGTAACCGGATGACGGTACAGGAACTGGCTGACCAGTTGTT 1560       1570       1580       1590       1600
      TCCCTACCTGACGATGGTCGAAGGGCTGAAGCTTGCTGCCCAGACCTTCA 1610       1620       1630
      CCAGGGATGTGAAGCAGTTGTCCTGCTGTGCGGGT
```

TABLE 4

Amino Acid Sequence

```
   1         10          20         30         40         50
   MTENAPTELAITGMTCDGCAAHVRKALEGVPGVREAQVSYPDATARVVLE 60          70         80         90        100
   GEVPMQRLIKAVVASGYGVHPRSDGASSTNDGQELHIAVIGTGGAAMACA 110         120        130        140        150
   LKAVERGARVTLIERSTIGGTCVNIGCVPSKIMIRAAHIAHLRRESPFDG 160         170        180        190        200
   GIQAVAPTIQRTALLVQQQARVDELRHAKYEGILDGNPAITVLRGEARFK 210         220        230        240        250
   DSRSVVVHLNDGGERVVMFDRCLVATGASPAVPPIPGLKDTPYWTSTEGL 260         270        280        290        300
   VSESIPERLAVIGSSVVALELAQAFARLGSHVTILARGTLFLREDPAIGE 310         320        330        340        350
   AITAAFRAEGIEVLEHTQASQVAYADGEFVLATGHGELRADKLLVATGRA 360         370        380        390        400
   PNTRRLNLEAAGVAINAQGAIVIDQGMRTNSPNIYAAGDCTDQPQFVYVA 410         420        430        440        450
   AAAGTRAAINMMGGSAALDLTAMPAVVFTDPQVATVGYSAEAHRDGIETD 460         470        480        490        500
   SRMTLDNVPRALANFNTRGFIKLVAEVGSGSLIGVQVVAPEAGELIQTAA 510         520        530        540
   LAIRNRMTVQELADQLFPYLTMVEGLKLAAQTFTRDVKQLSCCAG
```

The region of the nucleotide sequence shown in Table 3 which codes for the mercuric reductase contains a 1635-bp open reading frame and the mercuric reductase coded consists of 545 amino acid residues.

In order to confirm the initiation codon of the *T. ferrooxidans* merA gene, the mercuric reductase produced by pTM314 transformed *E. coli* was purified by affinity chromatography on Orange A martex (product of Amicon Co., Ltd.) The sequence of the 15 N terminal amino acids of this enzyme was determined with a gas-phase peptide sequencer Model 470A of Applied Biosystems, Inc. The determined amino acid sequence started with methionine and was completely homologous with the previously determined amino acid sequence. The results of comparison with other mercury resistance genes were as follows: *T. ferrooxidans* merA gene was homologous with Tn501 merA by 78.2% for DNA sequence and by 80.6% for amino acid sequence; the homology with R100 merA was by 80.8% for DNA sequence.

The results of these analyses show that the DNA fragments described above code for a mercuric reductase protein and can be used as selection markers for recombinant vectors in *T. ferrooxidans*.

In the next place, the present inventors prepared shuttle vector plasmids capable of replicating in either *T. ferrooxidans* or *E. coli*. Vectors must be capable of working as a replicon within the cells of *T. ferrooxidans*. The present inventors therefore prepared plasmids containing replication origins for both *T. ferrooxidans* and *E. coli* by linking an *E. coli* plasmid (pUC18 or PBR322) DNA with the plasmids derived from three *T. ferrooxidans* strains [pTSY91 (Y5-9, FERM BP-9157); pTSB121 (B-12, FERM BP-9156); and pTNA33 (MA3-3, FERM BP-10965)].

Plasmids pTSY91, pTSB121 and pTNA33 were respectively derived from *T. ferrooxidans* strains collected and isolated at the following three sites: Yanahara Mining Work, Dowa Mining Co., Ltd., Okayama; Kosaka Work of Barium Chemicals Co., Ltd., Akita; and former Matsuo Mine, Iwate. These plasmids have approximate sizes of 4.7 kb, 5.1 kb and 2.5 kb. respectively. Physical maps of these plasmids are shown FIGS. 10-12, respectively. These three plasmids deriving from *T. ferrooxidans* contain open reading frames but they are cryptic plasmids whose function is entirely unknown. In the complete absence of information about the locations and other characteristics of the replication origin for the Thiobacillus plasmids, the present inventors digested the plasmids at either one of the presumably symmetrical restriction enzyme cleavage sites with great care being taken not to cut at those replication origins. Stated more specifically, pTSY91 was cut at either PstI or EcoRV site, pTSB121 at either PstI or SalI site, and pTNA33 at either BamHI or KpnI site. If this method is employed, the replication origins are believed to be retained in at least either one of the two cleaved plasmid fragments.

The process of constructing plasmids having replication origins for *T. ferrooxidans* and *E. coli* is described below with reference to FIGS. 10–12:

cleaving pTSY91 and pUC18 with PstI and linking the resulting fragments together to construct pTY301;

cleaving pTSY91 and pBR322 with EcoRV and linking the resulting fragments together to construct pTY102;

cleaving pTSB121 and pUC18 with PstI and linking the resulting fragments together to construct pTB311;

cleaving pTSB121 and pUC18 with SalI and linking the resulting fragments together to construct pTB312;

cleaving pTNA33 and pUC18 with BamHI and linking the resulting fragments together to construct pTA321; and cleaving pTNA33 and pUC18 with KpnI and linking the resulting fragments together to construct pTA322.

Figure 8:
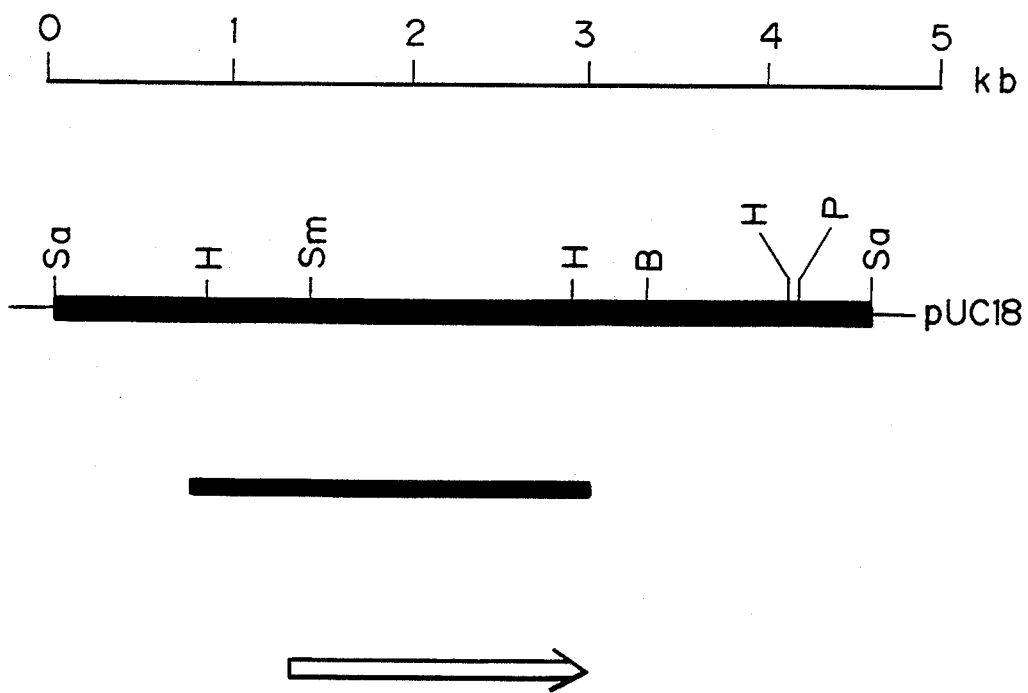
FIG. 8 is a physical map of a mercury resistance gene derived from T. ferrooxidans strain E-15.

In the next step, a DNA fragment coding for a *T. ferrooxidans* mercuric reductase is inserted into each of these vector plasmids to construct a shuttle vector that has a mercury resistance marker gene and that is capable of replicating in both *T. ferrooxidans* and *E. coli*. DNA fragments coding for a *T. ferrooxidans* mercuric reductase are isolated from the *T. ferrooxidans* derived plasmids, pTM314 and pTM315 (FIG. 10). In view of the restriction enzyme cleavage sites, plasmids pTM314 and pTM315 (FIG. 10) are used as a SalI fragment and a BamHI fragment, respectively. FIG. 8 is a physical map of the inserted DNA fragment of each of pTM314 and pTM315 digested with various restriction enzymes. In the figure, the direction of transcription is represented by the arrow and the region coding for the mercury resistance gene is represented by the thick solid line, with B referring to BamHI, H, HindIII, P, PstI, Sa, SalI, and Sm, SmaI. As shown in FIG. 8, both fragments entirely cover the sequence encoding the mercuric reductase.

Figure 10:
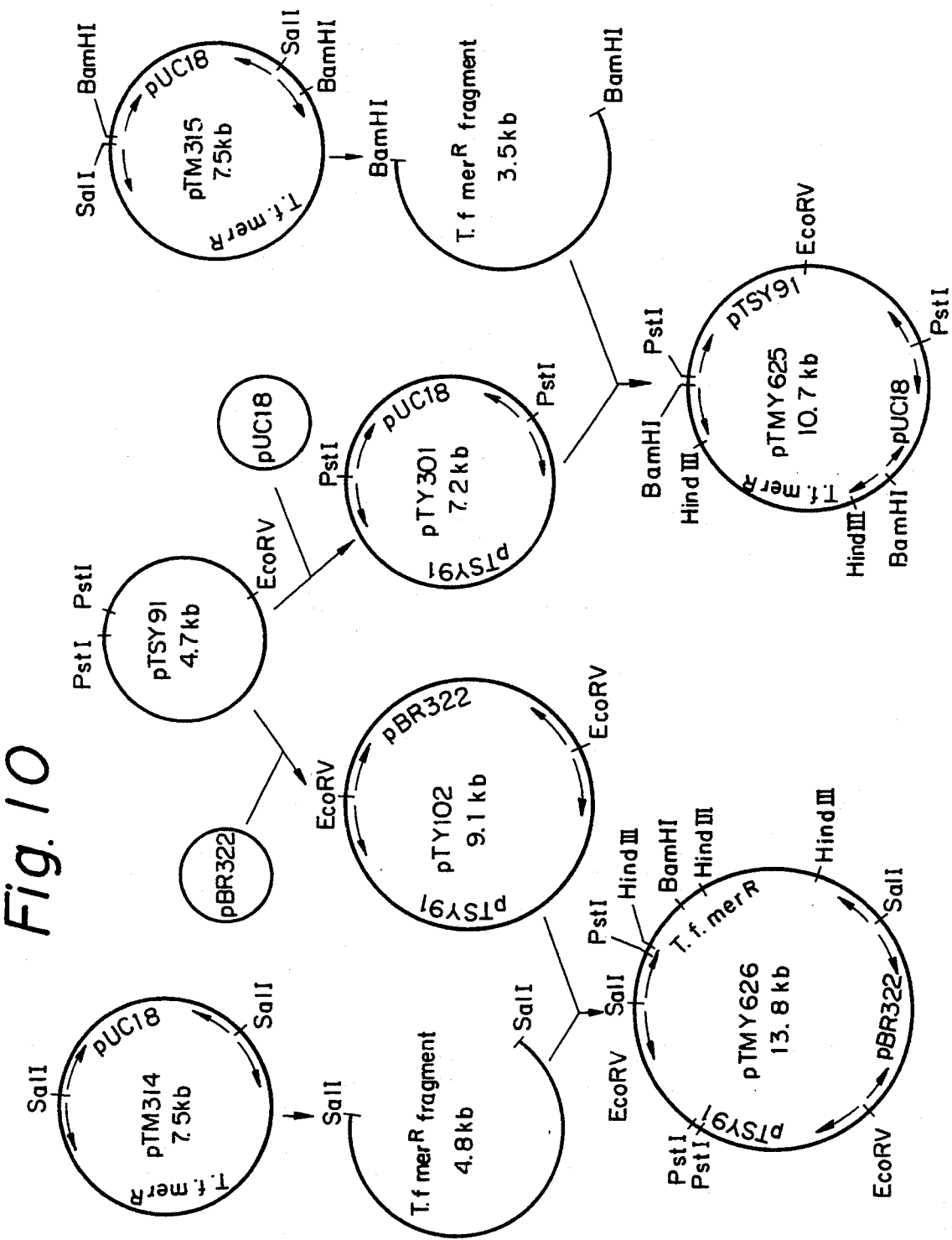
FIG. 10 shows the overall process of constructing novel shuttle vectors of the present invention by linking pTM314 with the Thiobacillus plasmid pTSY91 and E. coli plasmid pBR322 or by linking pTM315 with pTSY91 and E. coli plasmid pUC18.
Figure 11:
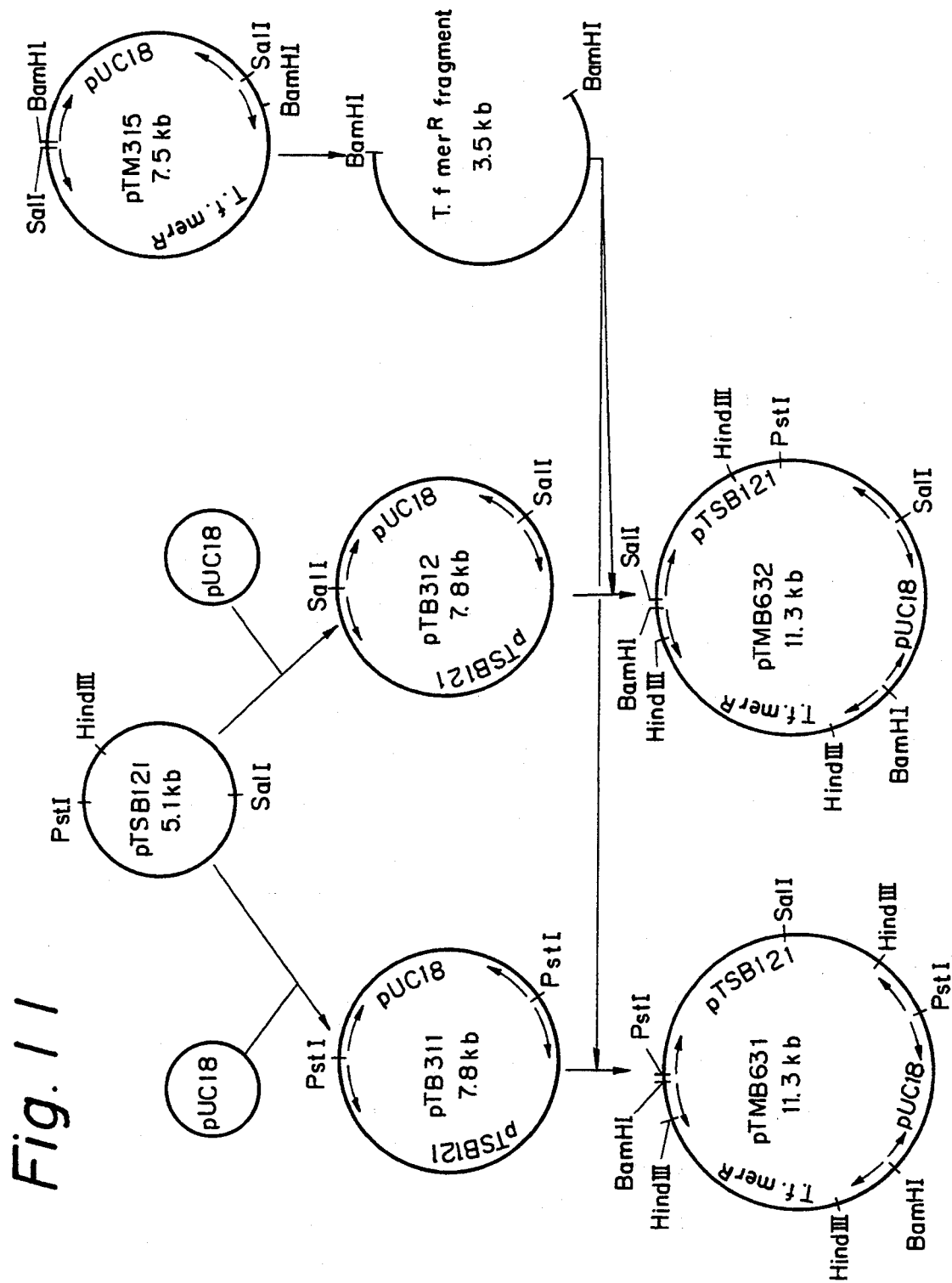
FIG. 11 shows the overall process of constructing novel shuttle vectors of the present invention by linking pTM315 with the Thiobacillus plasmid pTSB121 and E. coli plasmid pUC18.
Figure 12:
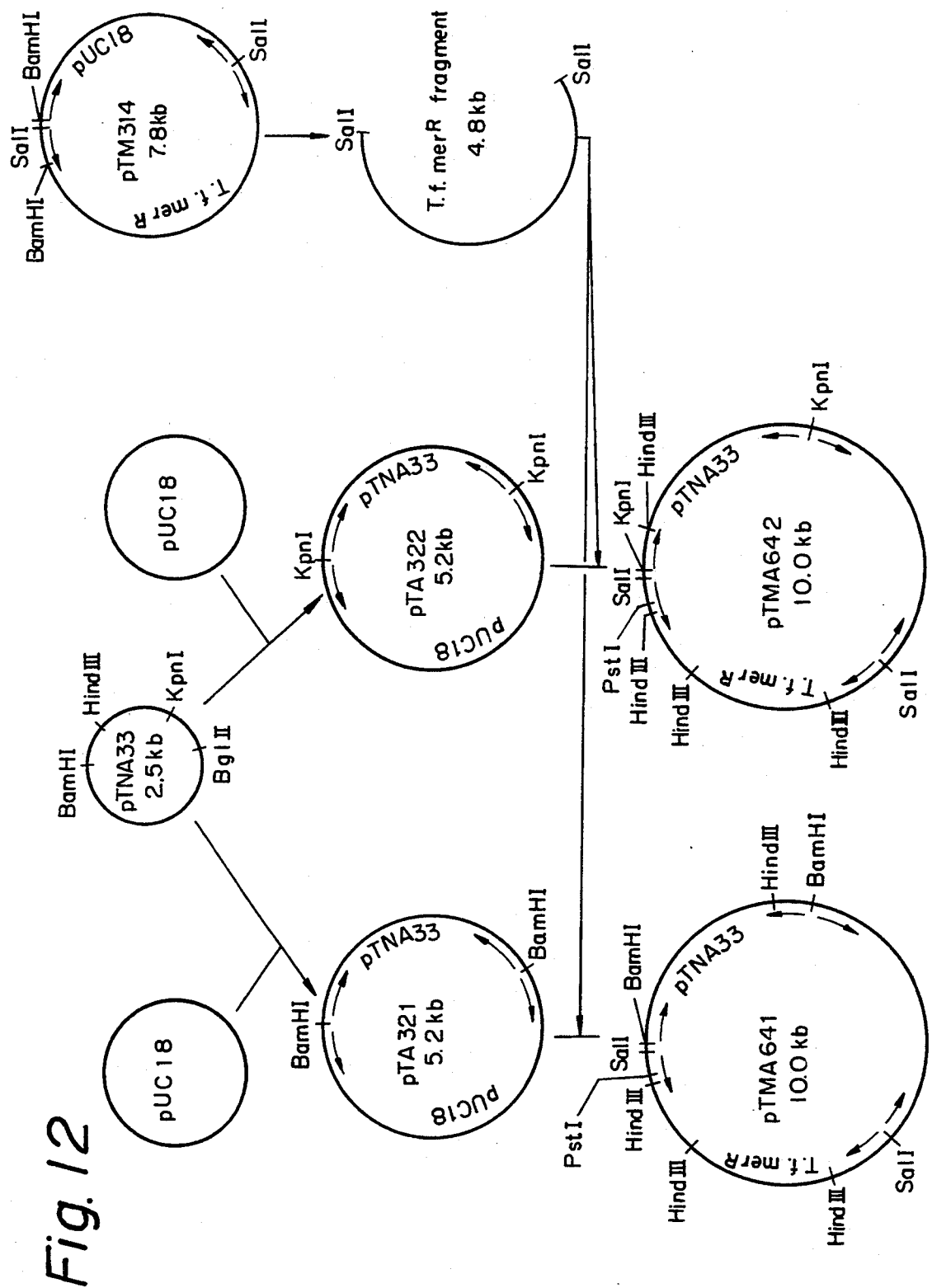
FIG. 12 shows the overall process of constructing novel shuttle vectors of the present invention by linking pTM314 with Thiobacillus plasmid pTNA33 and E. coli plasmid pUC18.

The process of constructing the desired shuttle vectors comprises the following:

cleaving the previously prepared pTY301 with BamHI and liking it with the BamHI-BamHI fragment of pTM315 to construct pTMY625 (FIG. 10);

cleaving pTY102 with SalI and linking it with the SalI-SalI fragment of pTM314 to construct pTMY626 (FIG. 10);

cleaving PTB311 with BamHI and linking it with the BamHI-BamHI fragment of pTM315 to construct pTMB631 (FIG. 11);

cleaving pTB312 with BamHI and linking it with the BamHI-BamHI fragment of pTM315 to construct pTMB632 (FIG. 11);

cleaving pTA321 with SalI and linking it with the SalI-SalI fragment of pTM314 to construct pTMA641 (FIG. 12); and cleaving pTA322 with SalI and linking it with the SalI-SalI fragment of pTM314 to construct pTMA642 (FIG. 12).

The so constructed shuttle vector plasmids contain a *T. ferrooxidans* mercury resistance gene marker and are capable of replicating in both *T. ferrooxidans* and *E. coli*.

In accordance with the present invention, the plasmid DNA is introduced into *T. ferrooxidans* cells by an electroporation technique, which comprises collecting host cells in the logarithmic growth phase, washing them, mixing them with a vector plasmid, and subjecting the mixture to electroporation by discharge of a 25-$\mu$F capacitor at a voltage of 6250 volts/cm, thereby transforming the host cells. This technique insures that at least 90% of the cells are viable after electroporation, with a gene introduction efficiency of ca. $10^5$ cells/$\mu$g DNA.

The host cells into which the *T. ferrooxidans* gene is to be introduced must be mercury-sensitive and should not have any restriction-modification system. Some wild strains of *T. ferrooxidans* contain one to several plasmids but host cells optimal for use in the present invention should contain no plasmid. It should however be noted that plasmid-containing host cells are acceptable as long as they are compatible with the plasmids of the present invention.

The novel shuttle vector plasmids of the present invention contain a replication origin for both *E. coli* and *T. ferrooxidans* and hence are capable of replicating in the cells of both species. Further, they contain a mercury resistance gene marker for the Thiobacillus genomic DNA cloned by the present inventors, and this enables selection for mercury-resistant strains in genetic manipulation experiments with *T. ferrooxidans*.

Stated more specifically, mercury-sensitive and resistant strains of *T. ferrooxidans* and *E. coli* are so different in MIC of $HgCl_2$ that selection for strains of interest can be made with mercury resistance being used as a criterion. With ordinary *E. coli* strains (mercury-ion sensitive strains) having no mercury resistance gene, the MIC of mercury ion is 5 $\mu$g/ml. In contrast, with an *E. coli* strain (mercury-ion resistant strain) into which a mercury resistance has been introduced, for example *E. coli* strain DH5$\alpha$ containing the *E. coli* plasmid pTM314 or pTM315 of the present invention, the MIC of mercury ion is not lower than 50 $\mu$g/ml. Therefore, mercury-sensitive and resistant *E. coli* strains can be separated by cultivating the cells in a medium containing $HgCl_2$ at concentrations of 15–20 $\mu$g/ml.

As for *T. ferrooxidans*, the MIC of mercury ion in mercury-sensitive strains is from 0.1 to 0.2 $\mu$g/ml, whereas it ranges from 0.75 to 1.0 $\mu$g/ml in resistant *T. ferrooxidans* strain E-15 having a mercury resistance gene in genomic DNA. Therefore, mercury-sensitive and resistant *T. ferrooxidans* strains can be separated by cultivating the cells in a medium containing $HgCl_2$ at a concentration of 0.3 $\mu$g/ml (see Example 10 provided hereinafter).

In the present invention, gene is incorporated by an electroporation technique. Since the cell wall is left intact in this technique, a high "cell survival rate" can be attained. In other words, the present invention provides a effective method of transforming Thiobacillus with high reproducibility.

The following examples are provided for the purpose of further illustrating the present invention but are in no way to be taken as limiting. As will be apparent to one skilled in the art, the procedures that can be employed in the present invention are not limited to those described below and various modifications and changes can be made without departing from the scope and spirit of the present invention. The restriction enzymes and media, as well as the methods of agarose gel electrophoresis, hybridization and transformation that were employed in the examples are first described below.

Enzyme Sources:

Restriction enzymes, AvaI, BamHI, BglII, EcoRI, EcoRV, HindIII, KpnI, PstI, SacI, SalI, SmaI and XbaI; DNA polymerase; Klenow fragment; exonuclease III; mung bean nuclease; CIP (alkali phosphatase); T4 DNA ligase. All these were commercially available and used in accordance with the instructions of the suppliers.

Media:

| A. 9K Medium of Silverman et al. | |
|---|---|
| (1) Inorganic Salt Solution | |
| $(NH_4)_2SO_4$ | 3 g |
| $K_2HPO_4$ | 0.5 g |
| $MgSO_4.7H_2O$ | 0.5 g |
| KCl | 0.1 g |
| $Ca(NO_3)_2$ | 0.01 g |
| Total | 700 ml |
| pH adjusted to 5.5 with $H_2SO_4$. | |
| (2) Ferrous Ion Solution | |
| $FeSO_4.7H_2O$ | 44.22 g |
| Total | 300 ml |
| pH adjusted to 1.4 with $H_2SO_4$. | |

Solutions (1) and (2) were autoclaved separately at 120° C. for 10 minutes, cooled and thereafter mixed to prepared 9K medium of Silverman et al.

| B. LB Medium (pH 7.5) | |
|---|---|
| Trypton | 1% |
| Yeast extract | 0.5% |
| NaCl | 1% |

Agarose Gel Electrophoresis:

An agarose gel was prepared by dissolving 0.7% agarose powder in a TAE buffer solution (40 mM Tris, 5 mM sodium acetate, 1 mM EDTA, ptI 7.8). After electrophoresis, the gel was submerged in an ethidium bromide solution (0.2 μg/mi) to stain the DNAs and fluorescent patterns were photographed with a Polaroid MP-4 Land camera under a UV lamp (302 nm).

Hybridization:

Dot and Southern hybridizations were performed using nylon filters (Biodyne A of Pall Corporation). In the southern method, DNAs were electroblotted onto the filter. Hybridization was done in the presence of 10% dextran sulfate (P. S. Thomas, Proc. Natl. Acad. Sci., USA. 77, 5201–5205, 1980). Each filter was finally washed with 0.1×SSC and 0.5% SDS (sodium dodecyl sulfate).

Colony hybridizations were performed by the protocol of Grunstein and Hogness (M. Grunstein and D. S. Hogness, Proc. Natl. Acad. Sol., USA 72, 3961–3965, 1975) using nylon membrane filters (BNNG 82 of Amersham Medical Limited or Biodyne A of Pall Corporation).

Transformation of E. coli:

E. coli DH5α was used as the transformation host.

Competent cells were prepared by the procedure of Hanahan (D. Hanahan, J. Mol. Biol., 166, 557–580, 1983). The efficiency of transformation of these competent cells was usually $10^7$ cells/μg of pUC18 DNA.

EXAMPLE 1

Screening of T. ferrooxidans Strains, MIC Measurements for Mercury Ion, and Mercury Volatilization Activity Measurements A. Screening of T. ferrooxidans Strains Samples of T. ferrooxidans were isolated from various mining sites in Japan. Cell suspensions were inoculated in the 9K medium or Silverman et al. (M. P. Silverman and D. G. Lundgren, J. Bateriol. 77, 642–647, 1959) and cultured. They were then cultured on colloidal silica gel plates (M. Kawarazaki, personal communication) to obtain single cell colonies.

The silica gel plates were prepared by the following procedure: 900 ml of colloidal silica No. 30 (Nissan Chemical Industries, Ltd.), 70 ml of 10-fold diluted 9K inorganic salt medium and 30 ml of saturated $FeSO_4.7H_2O$ solution were autoclaved separately, mixed together and adjusted to pH of 3.6 with $H_2SO_4$. After pouring 20-ml portions into petri dishes, heating was conducted at 60° C. for 16 hours to solidify the media, which had a pH of ca. 2.8.

T. ferrooxidans was identified taxonomically by comparison with the physiological characteristics listed in Bergey's Manual of Determinative Bacteriology, 8th ed.

As a result of the screening procedure described above, ten T. ferrooxidans strains, B-12, B-19, E-6, E-7, E-9, E-15, E-24, M4-6, U4-25 and Y5-9, were selected.

B. MIC Measurements for Mercury Ion

T. ferrooxidans strains, B-12, B-19, E-6, E-7, E-9, E-15, E-24, M4-6, U4-25 and Y5-9, were inoculated on the 9K medium and cultivated at 30° C. The grown clones were streaked onto colloidal silica gel plates containing $HgCl_2$ at varying concentrations of 0, 0.05, 0.1, 0.2, 0.3, 0.4, 0.5, 0.75, 1.0 and 1.5 μg/ml, followed by incubation at 30° C for 4 or 5 days. After the incubation, measurements were conducted for the MIC of $HgCl_2$ in each of the strains under test, the results of which are shown in Table 5.

TABLE 5

| | Strains | | | | | | | | | |
|---|---|---|---|---|---|---|---|---|---|---|
| | B-12 | B-19 | E-6 | E-7 | E-9 | E-15 | E-24 | M4-6 | U4-25 | Y5-9 |
| $HgCl_2$ (μg/ml) | 0.2 | 0.2 | 1.0 | 0.75 | 0.3 | 0.75 | 1.5 | 0.2 | 1.0 | 0.2 |

Among the strains under test, E-6, E-7, E-15, E-24 and U4-25 showed high MIC values, indicating that they were mercury-resistant strains.

For E. coli strain DH5α and DH5α carrying pUC18, MIC measurements were conducted by the serial dilution method in LB broth under aerobic conditions. The growth of the two strains was inhibited by $HgCl_2$ at a concentration of 5 μg/ml.

C. Measurements of Mercury Volatilization Activity

Preparing crude extracts of T. ferrooxidans:

T. ferrooxidans strains, E-6, E-7, E-15, E-24 and U4-25, were inoculated on the 9K medium and cultured at 30° C. The grown cells were cultured in 150 ml of the 9K medium of Silverman et al. in the presence of $HgCl_2$ at a concentration of 0.5 pg/ml and the cells in the stationary phase were harvested by centrifugation at 8,000 rpm for 20 minutes at 4° C. (Hitachi RPR 20-2 rotor). Subsequent operations were performed at 4° C. In order to remove the insolubles, in particular Fe(OH)SO$_4$, the harvested cells were washed twice with low-pH wash solution (9K inorganic salt medium containing 0.16 M MgSO$_4$.7H$_2$O; adjusted to pH 1.9 with H$_2$SO$_4$), then once with high-pH wash solution (25 mM phosphate buffer containing 0.3 M sucrose and 10 mM EDTA; pH 8.0), finally once with 50 mM phosphate buffer (pH 7.4). The cell pellets were resuspended in 1 ml of 50 mM phosphate buffer (pH 7.4) and disrupted with a Branson sonifier (setting 3, 20-second intervals, three times) on ice. The debris was removed by centrifugation at 12,000 rpm for 15 minutes and the supernatant was obtained as crude extracts.

Assay:

Assay solutions each having the recipe shown below were incubated at 37° C. for 20 minutes and the absorbance at 340 nm was measured.

| Assay Solution |
| --- |
| 50 mM K$_2$HPO$_4$—NaH$_2$PO$_4$ buffer (pH 7.4) |
| 0.5 mM EDTA |
| 0.2 mM MgSO$_4$ |
| 1 mM β-mercaptoethanol |
| 0.2 mM NADPH |
| 0.5 mg/ml BSA |
| 0.1 mM HgCl$_2$ |
| Crude extract (containing 5 μg of protein)* |
| Total: 100 μl |

*Amounts of protein in the extracts were measured by the Lowry method (O. H. Lowry et al., J. Biol. Chem. 193, 265-275, 1951).

The absorbance measured at 340 nm after the incubation was compared with the initial value and the differences were calculated to investigate the mercury-dependent oxidation of NADPH. The so obtained data on the mercury-dependent NADPH oxidation for each *T. ferrooxidans* strain under test are shown in Table 6. It should be noted here that NADPH of reduced type provides maximum absorption at 340 nm. If mercury ion is reduced to metallic mercury during the 20-minutes incubation, NADPH is oxidized to NADP in a mercury-dependent manner, giving larger values of Δ340 nm/20 min in Table 6. Therefore, the larger the values of Δ340 nm/20 min, the greater the degree of reduction of mercury ion to metallic form.

TABLE 6

| | Strains | | | | | | | | | |
| --- | --- | --- | --- | --- | --- | --- | --- | --- | --- | --- |
| | B-12 | B-19 | E-6 | E-7 | E-9 | E-15 | E-24 | M4-6 | U4-25 | Y5-9 |
| Δ340 nm/20 min$^{a)}$ | —$^{b)}$ | — | 0.97 | 1.35 | — | 1.02 | 0.12 | — | 0.07 | — |

$^{a)}$Values of Δ340 nm/20 min were determined by the following formula: (Initial absorbance at 340 nm) - (Absorbance at 340 nm after incubation at 37° C. for 20 min).
$^{b)}$Not tested.

The data provided in Tables 5 and 6 show that *T. ferrooxidans* strains E-6, E-7 and E-15 have both mercury resistance and mercury volatilizing activity. This result enabled the present inventors to conclude that *T. ferrooxidans* strains E-6, E-7 and E-15 exhibited mercury resistance on account of the presence of a mercuric reductase. These three strains of *T. ferrooxidans* were isolated at a hydrometallurgical processing workshop, Kosaka Refinery, Dowa Mining Co., Ltd. from the iron oxidizing step involving the use of iron oxidizing bacteria.

EXAMPLE 2

Recovery of Genomic DNA From *T. ferrooxidans*

Ten *T. ferrooxidans* strains, B-12, B-19, E-6, E-7, E-9, E-15, E-24, M4-6, U4-25 and Y5-9, were inoculated on 250 ml of the 9K medium of Silverman et al. and cultivated at 30° C. for 2 days. The cells of the culture were harvested by centrifugation and the cell pellets were washed with low-pH wash solution twice and with high-pH wash solution once. Subsequently, 4 ml of a solution consisting of lysozyme (2.5 mg/ml), 0.05 M glucose, 25 mM Tris-HCl (pH 8.0) and 10 mM EDTA was added and the mixture was left to stand at 0° C. for 10 minutes. Following the addition of 0.25 M EDTA (500 ml) and standing at 0° C. for 10 minutes, 500 ml of 10% SDS was added to effect lysis.

To the resulting solution. 50 ml of proteinase K was added at a concentration of 20 mg/ml, followed by 2-hour incubation at 37° C. to decompose the protein.

The homogenate was deproteinlzed with an equal volume of phenol:chloroform (1:1) mixture three times. By treatment with isopropanol, the nucleic acid portion was precipitated, and the precipitate was collected by centrifugation and dried.

For further purification, density gradient centrifugation with cesium chloride (20° C, 55,000 rpm, 16 hours) and dialysis (24 hours) were conducted to obtain purified genomic DNA fractions.

EXAMPLE 3

Dot Hybridization of *T. ferrooxidans* Genomic DNA

Five micrograms each of the genomic DNAs prepared in Example 2 was blotted onto a nylon membrane filter (Biodyne A of Pall Corporation). The DNA fractions on the filters were denatured, neutralized and baked at 80° C. for 1 hour to be permanently bound to the filter. These procedures were taken in accordance with the molecular cloning method of Maniatis et al. (T. Maniatis et al. "Molecular Cloning—A Laboratory Manual", Cold Spring Harbor Laboratory. 1982). After prehybridization, the $^{32}$P-labeled DNA probe prepared by the method described below was added in the presence 10% dextran sulfate and incubation was done at 65° C. for 20 hours. The filters were washed with 0.1×SSC and 0.5% SDS at 65° C. Autoradiographs were taken with an intensifying screen at −80° C. The autoradiogram obtained is shown in FIG. 1, from which one can see the presence of a mercury resistance gene in the genome of each of *T. ferrooxidans* strains E-6, E-7 and E-15.

Preparation of $^{32}$P-labeled probes:

Pseudomonas PA025 derived plasmid pME285 was digested with AvaI and HindIII to obtain a DNA fragment (mer$^R$) coding for a Tn501 mercury resistance gene. The mer$^R$ fragment (4.5 kb from the AvaI-HindIII site of pME285) was blunted with Kienow fragment, tagged with BamHI linker (Takara Shuzo Co.)

and thereafter subcloned in pBR322. The resulting plasmid was named pM610.

The $mer^R$ fragment was cut out from pM610, recovered by electroelution with a dialysis tube, and subjected to nick translation which was performed as follows: a mixture of 0.1–0.5 μg of DNA fragment, 50 μCi of [α-$^{32}$P]dCTP (3,000 Ci/mmol; Dupont, NEN Research Products or Amersham Medical Limited), 1 ng/ml of DNaseI (endonuclease), 20 μm each of dATP, dTTP, dGTP and E. coli DNA polymerase I (10 units) was incubated at 20° C. for 2 hours. Unincorporated [$^{32}$P]dCTP was eliminated with a Sephadex G-50 minicolumn (1.0×10 cm).

EXAMPLE 4

Southern Hybridization of T. ferrooxidans Genome and Tn501 Mercury Resistance Gene Each of the genomic DNAs isolated from T. ferrooxidans strains E-6, E-7 and E-15 prepared in Example 2 was cleaved with HindIII-EcoRI and SalI, and 5 μg of each fragment was subjected to electrophoresis through 0.7% agarose gel. Subsequent operations that preceded Southern hybridization, namely, DNA depurination, denaturation, neutralization on gel, blotting onto nylon membrane filters (Biodyne A of Pall Corporation) and baking (80° C.×2 hours) were performed accordance with the molecular cloning method of Maniatis et al.

The $^{32}$P-labeled DNA probe prepared by nick translation as described in Example 3 was hybridized with the genomic DNAs fixed to the membrane filters in the presence of 10% dextran sulfate and subsequently washed with 0.1×SSC and 0.5% SDS at $65_2$ C. Autoradiographs were taken and the autoradiogram obtained is shown in FIG. 2, in which the length of size markers is indicated in kilobase pairs on the vertical axis and the type of genomic DNA fragment is indicated by lanes 1–6 on the horizontal axis. Lanes 1–3 refer to HindIII-EcoRI fragments and lanes 4–6 refer to SalI fragments. Lanes 1 and 4 represent T. ferrooxidans strain E-6, lanes 2 and S, strain E-7, and lanes 3 and 6, strain E-15.

As is clear from FIG. 2, the three T. ferrooxidans strains had different positions of hybridization between genomic DNA and probe, suggesting that those strains had different mercuric reductase genes.

EXAMPLE 5

Cloning of Mercuric Reductase Gene Contained in the Genomic DNA of T. ferrooxidans Strain E-15

Figure 3:
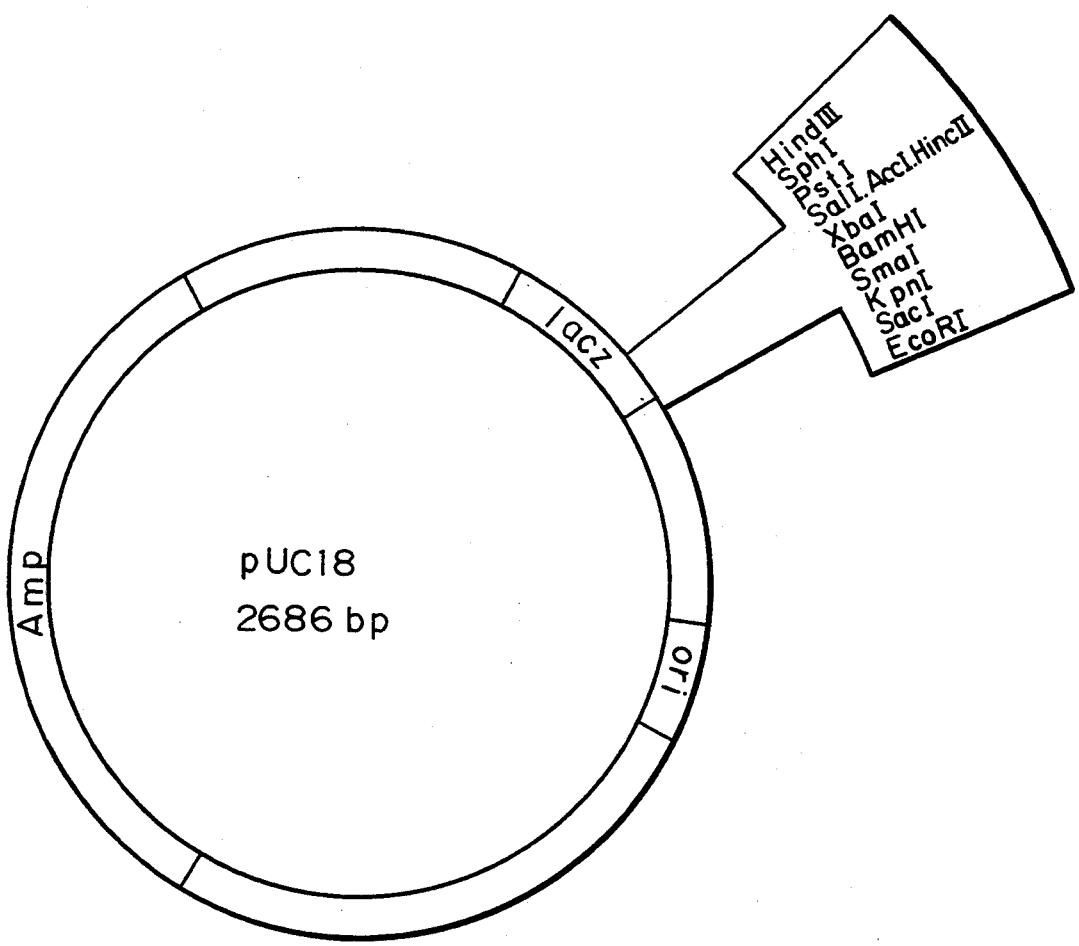
FIG. 3 is a physical map of E. coli plasmid pUC18.

One microgram of the E-15 genomic DNA prepared in Example 2 was cleaved with restriction enzyme SalI (Takara Shuzo Co., Ltd.) (the fragment cut out is hereunder referred to as Thiobacillus $mer^R$ fragment) and linked to 0.2 μg of the DNA of SalI digested E. coli plasmid pUC18 (whose physical map is shown in FIG. 3) with T4 DNA ligase. The ligated DNA mixture was incorporated into the cells of E. coli DH5α, which were streaked into a plate LB medium (1.5% agar) containing 50 μg/ml of ampicillin, 40 μg/ml of X-gal and 1 mM of isopropyl-β-D-thiogalactopyranoside, and thereafter cultured at 37° C. for 24 hours.

E. coli DH5α carrying pUC18 should normally yield blue colonies but upon insertion of a heterologous DNA at the linker cloning site, it will lose its ability to produce pigments and form white colonies on the plate medium described above. On the basis of this fact, colonies carrying a plasmid that had a heterologous DNA inserted at the linker cloning site of pUC18 were selected by confirming their white color. Of the about 2,000 colonies formed, about 500 had a heterologous DNA inserted at the linker cloning site of pUC18.

These colonies were transferred onto nylon membrane filters (BNNG 82) and subjected to colony hybridization with the probe being 32P-labeled Tn501 mercury resistance gene that had been prepared as described in Example 3.

The autoradiogram obtained showed that two colonies hybridized with the probe. The plasmids In these positive colonies were named pTM314 and pTM315. Electrophoretic patterns of these plasmids are shown in FIG. 6. The numerals on the left vertical axis of FIG. 6 represent the length of size marker in kilobase pairs. Symbol A on the right vertical axis represents the fragment inserted in pTM314 (for its physical map, see FIG. 4) between two BamHI sites (extending from near scale 4 to near scale 5 in clockwise direction), and symbol B represents the remaining fragment. Symbol C represents the fragment inserted in pTM315 (for physical map, see FIG. 5) between two BamHI sites (extending from near scale 4 to near scale 0 in counterclockwise direction), and symbol D represents the remaining fragment. Numeral 1 on the top horizontal axis represents the size marker of λ phage cleaved with HindIII (λ phage/HindIII); 2 uncleaved pTM314; 3 pTM314/SalI; 4 pTM314/BamHI; 5 pTM315/BamHI; 6 pTM314/HindIII; and 7 pTM315/HindIII.

Figure 4:
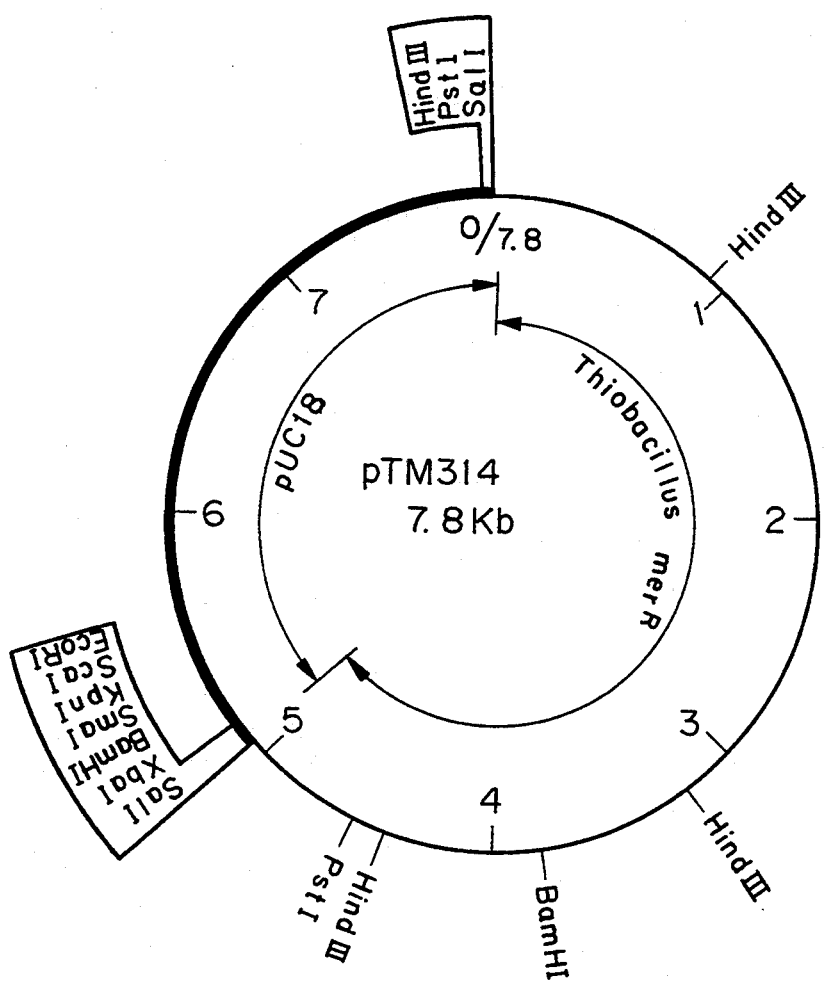
FIG. 4 is a physical map of a novel plasmid pTM314 of the present invention.
Figure 5:
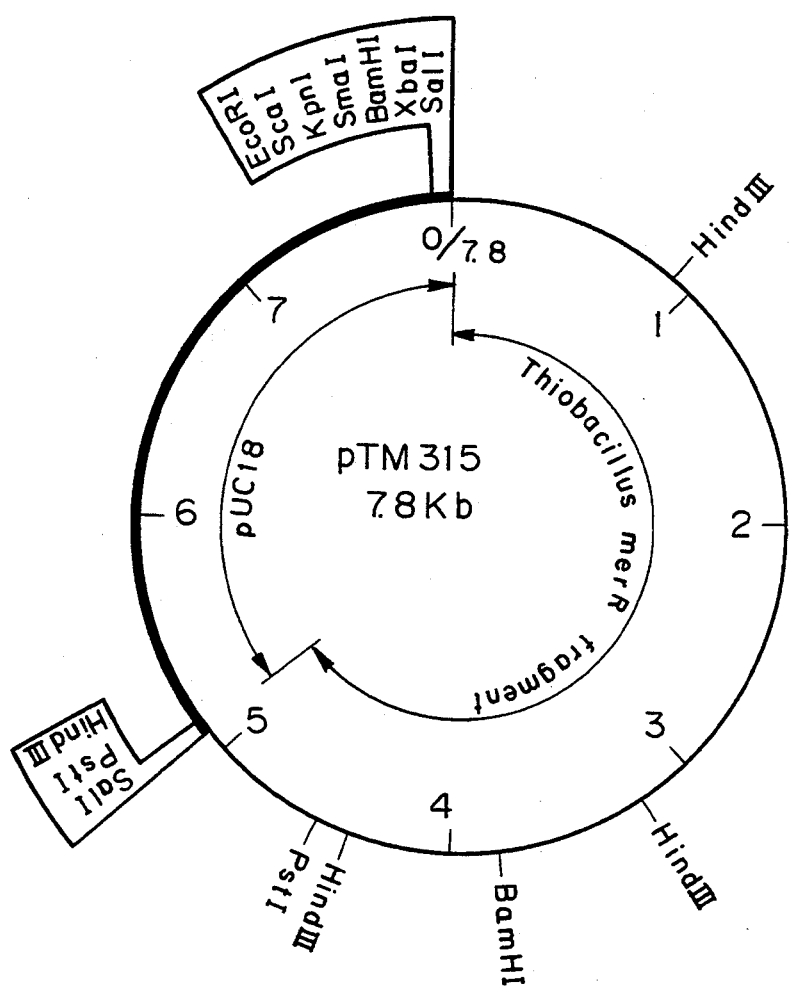
FIG. 5 is a physical map of a novel plasmid pTM315 of the present invention.
Figure 6:
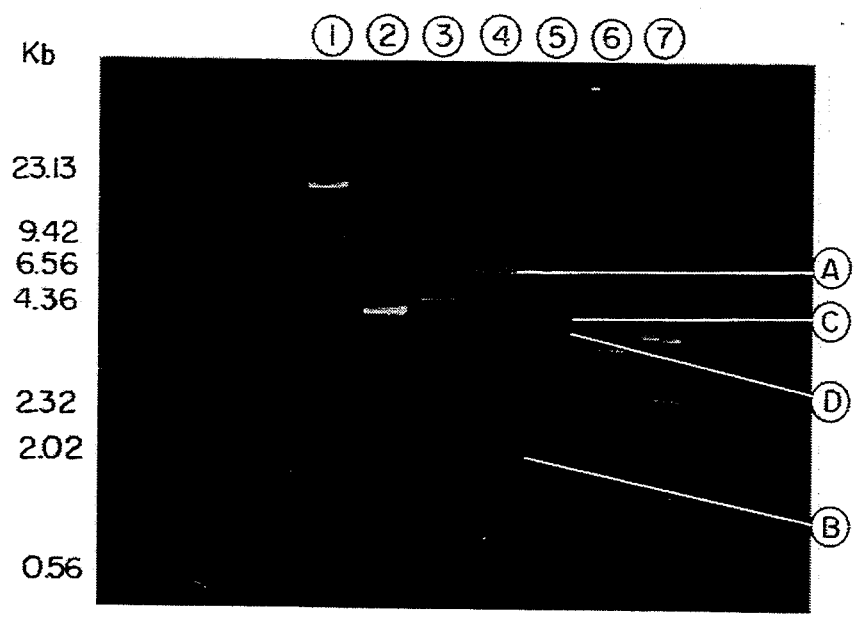
FIG. 6 is a picture showing the electrophoretic patterns of pTM314, pTM315 and various DNA fragments cut therefrom.

Since pTM314 and pTM315 have the Thiobacillus $mer^2$ fragment inserted in opposite directions with respect to pUC18, they will produce different cut patterns when digested with appropriate restriction enzymes (see FIGS. 4 and 5). If they are digested with BamIII, fragments represented by A–D will result, and similar results will occur if they are digested with hindIII. As a consequence, pTM314 and pTM315 produce different electrophoretic patterns as shown in FIG. 6.

EXAMPLE 6

A. Construction of Deletion Plasmids

Samples of 2 μg of pTM314 and pTM315 were digested with XbaI and SacI. The linearized fragments were digested with exonuclease III at 60-second intervals for 20 minutes. The digested mixtures were blunt ended with mung beam nuclease, followed by treatment with the Klenow fragment to ensure complete blunting. Ligation with T4 DNA ligase was done at 16° C. for 16 hours. The ligated samples were cleaved with XbaI and incorporated into E. coli DH5α. About 200 clones each of the transformants were analyzed and a series of plasmids with deletions of every ca. 300 bp were selected. Sixteen deletion plasmids originating from pTM314 were named, in order, pTM401 to pTM416. For pTM315, 15 deletion plasmids were named pTM501 to pTM515.

The SalI-BamIII, SalI-PstI, SalI-HindIII, HindIII-SalI, HindIII-HindIII and HindIII-BamHI fragments of pTM314 were linked to the polylinker site of pUC18 to construct deletion plasmids, which were respectively named pTM351, pTM352, pTM362, pTM364, pTM368 and pTM371.

The physical maps of the constructed deletion plasmids are shown in FIG. 7.

B. Detection of Bacterial Volatilization of Mercuric Chloride

Plasmids pTM314, pTM315 and their deletion plasmids (pTM351, pTM352, pTM362, pTM364, pTM368, pTM371, pTM405 to pTM408, pTM502 to pTM505)

were tested for their mercury volatilizing activity by the following procedures.

The plasmids were incorporated into *E. coli* DH5α and cultured in Luria broth containing 2.5 μg of HgCl$_2$ per ml. Subsequently, each culture was streaked onto a Luria agar plate containing 1 μg of HgCl$_2$ per ml and cultured overnight at 37° C. On the next day, individual cell masses were collected with a toothpick and resuspended in 50 μl of a reaction solution in the wells of a 96-well microtiter plate, which reaction solution consisted of 1/15 M phosphatic buffer (pH 7.0), 0.5 mM EDTA, 0.2 mM magnesium acetate, 5 mM sodium tioglycolate, and 20–40 ppm of HgCl$_2$. Immediately thereafter, an X-ray film (Kodak X-OMAT AR) and an acrylic plate were sequentially mounted over each microtiter plate in the dark and both ends were fixed with clips. The plate was then put into a dark box and incubated for 60 minutes at 37° C. After the incubation, the X-ray film was developed. The result is shown on the right-hand side of FIG. 7. The fogged areas on the film reflect the reduction of the Ag$^+$emulsion by mercury vapor.

C. MIC Measurements for Mercury Ion

The MIC of mercury ion in *E. coli* DH5α that had been transformed with each of the plasmids prepared in step B was measured by the same method as described in Example 1-B. The results are shown in Table 7.

TABLE 7

| Plasmid | HgCl$_2$ (μg/ml) |
|---|---|
| pTM314 | 50 |
| pTM351 | 50 |
| pTM352 | 50 |
| pTM362 | 5 |
| pTM364 | 10 |
| pTM368 | 5 |
| pTM371 | 10 |
| pTM405 | 50 |
| pTM406 | 50 |
| pTM407 | 5 |
| pTM408 | 5 |
| pTM502 | 50 |
| pTM503 | 50 |
| pTM504 | 5 |
| pTM505 | 5 |

The above data and the physical maps of the deletion plasmids shown in FIG. 7 seem to warrant the conclusion that mercury resistance would be exhibited by the 2.3-kb region spanning the 2.1-kb HindIII fragment.

D. Analysis of Plasmid-produced Proteins by the Maxicell Method

Among the plasmids that were found to have mercury ion MICs of at least 10 μg/ml, pTM314, pTM315, pTM351, pTM352, pTM364, pTM371 and pTM362 were isolated by means of transformed *E. coli* CSR603.

*E. coli* CSR603 having pTM314, pTM315 or deletion plasmids thereof incorporated were cultured in K medium (M9 medium supplemented with 1% Casamino acids and 0.1 μg/ml of thiamine) aerobically at 37° C.

After UV irradiation (50 J/m$_2$) for 45 seconds, cells were treated with D-cycloserine (150 μg/ml).

Maxicell proteins (plasmid-produced proteins) were labeled with [$^{35}$S]methionine (1,000 Ci/mmol; Dupont, NEN Research Products) in accordance with the method of Sancar et al. (A. Sancar et al., J. Bacteriol. 137, 692–693, 1979). Gel electrophoresis was performed by the method of Laemmli [U. K. Laemmli, Nature (London) 227, 680–685, 1970], and sodium sailcylate was used for detection of the $^{35}$S-labeled polypeptide.

As a control, *E. coil* CSR603 carrying pUC18 was treated by similar procedures to detect maxicell proteins.

Thus, the proteins produced by plasmids pUC18, pTM315, pTM351, pTM364 and pTM371 were detected and separated by gel electrophoresis (FIG. 9).

As a result, it was found that the 2.3-kb region spanning the 2.1-kb HindIII region encoded two kinds of polypeptide with different molecular weights, 56 kDa and 16 kDa. Since the merA gone products of R100 and Tn501 have molecular weights of 58,905 and 58,727 daltons, respectively, it was speculated that the polypeptide with a molecular weight of 56 kDa should be a mercuric reductase.

EXAMPLE 7

Analysis of the Nucleotide Sequence of DNA Coding for *T. ferrooxidans* Mercuric Reductase and Analysis of Said Reductase For sequence analysis, deletion plasmids were prepared from pTM314 and pTM315 by the following procedures.

First, 1.5-kb SalI-SmaI, 3.1-kb SmaI-SalI, 1.6-kb SalI-HindIII and 3.0-kb HindIII-SalI fragments were recloned at the polylinker site of pUC18. The inserts in subcloned plasmids were treated with exonuclease III to prepare deletion plasmids with orderly deletions at intervals of ca. 300 bp.

Sequencing reactions were carried out using the denatured plasmid templates (Hattori and Sakaki, 1986) by the dideoxynucieotlde chain-termination procedure (the Sanger method). This was performed with a 7-deaza sequencing kit (Takara Shuzo Co., Ltd.) containing dc$^7$dGTP instead of dGTP and [$-^{32}$P]dCTP (Amersham or NEN, 400 Ci/mmole). Primer M1 (15 mer; 5'-AGTCACGACGTTGTA-3') and primer RV (17 mer; 5'-CAGGAAACAGCTATGAC-3'), which hybridized 16 bp upstream from the HindIII site and 8 bp upstream from the EcoRI site of pUC18, respectively, were purchased from Takara Shuzo Co., Ltd.

Sequencing Analysis:

The nucleotide and amino acid sequences were analyzed with SDC-GENETYX genetic information processing programs (Software Development Co., Ltd.)

The so determined nucleotide sequence of the DNA fragment coding for *T. ferrooxidans* mercuric reductase is shown below, followed by the determined amino acid sequence of that reductase.

| Nucleotide Sequence | | | | |
|---|---|---|---|---|
| 1 | 10 | 20 | 30 | 40 | 50 |
| ATGACCGAGAACGCGCCCACCGAACTCGCTATCACTGGCATGACCTGCGA | | | | |
| 60 | 70 | 80 | 90 | 100 |
| CGGTTGCGCCGCGCATGTGCGCAAAGCACTCGAAGGCGTGCCCGGCGTAC | | | | |
| 110 | 120 | 130 | 140 | 150 |
| GCGAGGCGCAGGTGTCCTACCCGGATGCCACGGCCCGGGTCGTGCTGGAG | | | | |

-continued

Nucleotide Sequence

```
        160         170         180         190         200
GGCGAGGTGCCGATGCAGCGGCTAATCAAGGCGGTGGTTGCAAGTGGCTA 210         220         230         240         250
TGGTGTGCATCCACGGAGCGACGGTGCCTCCTCCACAAACGATGGACAGG 260         270         280         290         300
AGCTACACATCGCTGTGATCGGCACCGGCGGAGCGGCGATGGCGTGCGCA 310         320         330         340         350
TTGAAGGCTGTCGAGCGGGGCGCGCGCGTGACGCTGATCGAACGCAGCAC 360         370         380         390         400
CATCGGCGGCACCTGCGTGAACATCGGTTGCGTGCCGTCCAAGATCATGA 410         420         430         440         450
TCCGCGCCGCCCATATCGCCCACCTCCGCCGGGAAAGCCCATTCGATGGC 460         470         480         490         500
GGCATCCAGGCGGTCGCGCCGACCATCCAGCGCACAGCGCTGCTGGTCCA 510         520         530         540         550
ACAGCAGGCCCGTGTCGATGAACTGCGTCACGCCAAGTACGAAGGCATCC 560         570         580         590         600
TGGACGGCAACCCGGCCATCACCGTTCTGCGCGGTGAAGCGCGTTTCAAG 610         620         630         640         650
GACAGCCGGAGTGTTGTCGTCCATTTGAACGATGGTGGCGAGCGCGTCGT 660         670         680         690         700
AATGTTCGACCGCTGCCTGGTTGCCACGGGCGCCAGTCCGGCCGTGCCGC 710         720         730         740         750
CGATTCCCGGCTTGAAAGACACTCCTTATTGGACCTCCACCGAAGGGCTG 760         770         780         790         800
GTCAGCGAATCGATCCCCGAGCGTCTGGCCGTGATCGGCTCGTCGGTGGT 810         820         830         840         850
GGCGCTGGAACTGGCGCAAGCCTTCGCCCGGCTCGGCAGCCATGTGACGA 860         870         880         890         900
TCCTGGCGCGCGGCACCTTGTTCCTCCGGGAAGACCCGGCCATCGGTGAG 910         920         930         940         950
GCCATCACGGCGGCGTTTCGCGCCGAAGGCATCGAGGTGCTGGAGCACAC 960         970         980         990        1000
CCAGGCCAGCCAGGTCGCTTATGCGGATGGCGAATTTGTGCTAGCCACCG 1010        1020        1030        1040        1050
GGCACGGCGAACTGCGCGCCGATAAGCTGCTGGTCGCCACTGGTCGCGCA 1060        1070        1080        1090        1100
CCGAACACACGCCGCCTGAATCTGGAAGCGGCGGGCGTGGCCATCAATGC 1110        1120        1130        1140        1150
GCAAGGGGCCATCGTCATCGACCAGGGTATGCGCACGAACAGCCCGAACA 1160        1170        1180        1190        1200
TTTACGCCGCTGGCGACTGCACCGACCAGCCGCAATTCGTCTACGTGGCG 1210        1220        1230        1240        1250
GCAGCGGCCGGCACCCGTGCGGCCATCAACATGATGGGCGGTAGTGCAGC 1260        1270        1280        1290        1300
CCTGGACTTGACGGCGATGCCAGCCGTGGTGTTCACCGATCCGCAAGTGG 1310        1320        1330        1340        1350
CGACTGTGGGTTACAGCGCGGAAGCGCATCGCGACGGCATCGAAACCGAC 1360        1370        1380        1390        1400
AGCCGCATGACGCTCGACAACGTGCCGCGGGCGCTCGCCAATTTCAATAC 1410        1420        1430        1440        1450
ACGCGGCTTCATCAAGCTGGTAGCCGAAGTGGGCAGTGGCTCGCTAATCG
```

-continued

Nucleotide Sequence

```
         1460       1470       1480       1490       1500
GCGTGCAGGTGGTCGCCCCGGAAGCGGGCGAGCTGATCCAGACTGCCGCG 1510       1520       1530       1540       1550
CTGGCGATTCGTAACCGGATGACGGTACAGGAACTGGCTGACCAGTTGTT 1560       1570       1580       1590       1600
TCCCTACCTGACGATGGTCGAAGGGCTGAAGCTTGCTGCCCAGACCTTCA 1610       1620       1630
CCAGGGATGTGAAGCAGTTGTCCTGCTGTGCGGGT
```

Amino Acid Sequence

```
1        10         20         30         40         50
MTENAPTELAITGMTCDGCAAHVRKALEGVPGVREAQVSYPDATARVVLE 60         70         80         90        100
GEVPMQRLIKAVVASGYGVHPRSDGASSTNDGQELHIAVIGTGGAAMACA 110        120        130        140        150
LKAVERGARVTLIERSTIGGTCVNIGCVPSKIMIRAAHIAHLRRESPFDG 160        170        180        190        200
GIQAVAPTIQRTALLVQQQARVDELRHAKYEGILDGNPAITVLRGEARFK 210        220        230        240        250
DSRSVVVHLNDGGERVVMFDRCLVATGASPAVPPIPGLKDTPYWTSTEGL 260        270        280        290        300
VSESIPERLAVIGSSVVALELAQAFARLGSHVTILARGTLFLREDPAIGE 310        320        330        340        350
AITAAFRAEGIEVLEHTQASQVAYADGEFVLATGHGELRADKLLVATGRA 360        370        380        390        400
PNTRRLNLEAAGVAINAQGAIVIDQGMRTNSPNIYAAGDCTDQPQFVYVA 410        420        430        440        450
AAAGTRAAINMMGGSAALDLTAMPAVVFTDPQVATVGYSAEAHRDGIETD 460        470        480        490        500
SRMTLDNVPRALANFNTRGFIKLVAEVGSGSLIGVQVVAPEAGELIQTAA 510        520        530        540
LAIRNRMTVQELADQLFPYLTMVEGLKLAAQTFTRDVKQLSCCAG
```

In order to confirm that start codon of *T. ferrooxidans*, the mercuric reductase isolated from pTM314 transformed *E. coli* was purified by affinity chromatography (Orange A martex, Amicon Co., Ltd.) and the sequence of the 15 N terminal amino acids was determined with a gas-phase peptide sequencer (Applied Biosystems Inc.) The enzyme interest was found to have an amino acid sequence starting with methionine, which was completely identical to the amino acid sequence of mercuric reductase shown in the previous paragraph.

EXAMPLE 8

Recovery of Plasmid DNAs From *T. ferrooxidans*

Strains of *T. ferrooxidans* carrying plasmids pTSY91, pTSB121 and pTNA33 (strains Y5-9, B-12 and MA3-3 deposited with the Fermentation Research Institute, the Agency of Science and Technology under accession numbers FERM BP-9157, FERM BP-9156 and FERM BP-10965, respectively) were cultivated In about 9 l of 9K medium, harvested by centrifugation and washed successively with low-pH wash solution, high-pH wash solution.

Plasmids were recovered by the alkali SDS method which was modified as follows: cell pellets having a wet weight ca. 1 g were suspended in 4 ml of Solution I [50 mM glucose, 25 mM Tris-HCl (pH 8.0) and 10 mM EDTA] containing 10 mg/ml of lysozyme and incubated at room temperature for 5 minutes. Then, 8 ml of Solution II (0.2 N sodium hydroxide and 1% SDS) was added and incubated at 4° C. for 5 minutes. Thereafter, 6 ml of Solution III (60 ml of 5 M potassium acetate, 11.5 ml of glacial acetic acid, 28.5 ml of water; pH 5.2) was added and incubated at 4° C. for 5 minutes. The mixture was then centrifuged at 15,000 rpm for 10 minutes at 4° C.

The supernatant was treated with phenol to remove proteins, followed by addition of Isopropyl alcohol to precipitate nucleic acids. Plasmid DNA was collected by centrifugation and dried.

For further purification, the sample was subjected to density gradient centrifugation (20° C., 55,000 rpm × 16 hours) with cesium chloride.

EXAMPLE 9

Construction of Shuttle Vector Plasmids

A. Constructing a Plasmid Having Replication Origins for Thiobacillus Derived Plasmid and E. coli Derived Plasmid In order to create a replication origin for Thiobacillus plasmid, the plasmid DNA of pTSY91 prepared in Example 8 was cleaved with either PstI or EcoRV which were restriction enzymes having cleavage sites on symmetrically positions. In the next step, E. coli plasmid pBR322 was digested with EcoRV, and pUC18 with PstI.

The so prepared Thiobacillus derived plasmid DNA and E. coli derived plasmid DNA were linked with T4 ligase. Ligation was conducted by the following two combinations: pTSY91-EcoRV and pBR322-EcoRV; or pTSY91-PstI and pUC18-PstI. In either combination, Thiobacillus plasmid derived DNA and E. coli plasmid derived DNA were used in respective amounts of 0.5 μg and 0.05 μg.

The resulting hybrid DNAs were mixed with CaCl$_2$-treated E. coli DH5α and low temperature to transform it.

The cells transformed with vector pBR322-EcoRV and pTSY91-EcoRV ligated were streaked onto a solid medium containing 50 μg/ml of ampicillin and cultured. The resulting colonies were transferred onto a solid medium containing 12.5 μg/ml of tetracycline and selected for ampicillin resistance and tetracycline sensitivity. Plasmids were extracted from the positive clones, followed by electrophoretic separation and purification to obtain recombinant plasmid pTY102 (9.1 kb).

The cells transformed with vector pUC18-PstI and pTSY91-PstI ligated were streaked onto a solid medium containing 50 μg/ml of ampicillin, 0.4 μg/ml of X-gal (5-bromo-4-chloro-3-indolyl-β-D-galactopyranoside) and 100 mM IPTG (isopropyl-β-D-thiogalactopyranoside). On account of the insertion of Thiobacillus derived plasmid DNA, pUC18 lacZ gene had been cleaved to yield colonies that did not produce a blue pigment upon cultivation on said medium. Such negative colonies were selected and the extracted plasmids were separated and purified by electrophoresis to obtain recombinant plasmid pTY301 (7.2 kb).

B. Incorporation of DNA Fragments Coding for T. ferrooxidans Mercuric Reductase Gene Plasmids pTM314 and pTM315 were digested with SalI and BamHI, respectively, to obtain DNA fragments (4.8 kb and 3.5 kb) coding for T. ferrooxidans mercuric reductase gene. After purification, these fragments were subjected to the following experiment.

Recombinant plasmids pTY102 and pTY301 prepared in step A were digested with SalI and BamHI, respectively. A 0.05-μg portion of pTY102-SalI fragment (or pTY301-BamHI fragment) was mixed with 0.5 μg of pTM314-SalI fragment (or PTM315-BamHI fragment) and linked by means of T4-DNA ligase.

The so obtained hybrid DNA was mixed with CaCl$_2$-treated E. coli DH5α at low temperature to transform it. The transformant cells were streaked onto a solid medium containing 50 μg/ml of ampicillin and cultured. Grown colonies were transferred onto nylon membrane filters, on which lysis, DNA denaturation and baking were conducted. Thereafter, hybridization was conducted using as a probe the Tn501 mer$^R$ fragment labeled with $^{32}$P-dCTP by nick translation. Plasmids containing Thiobacillus mer$^R$ fragments which produced shadow in an X-ray film were selected and named pTMY626 (13.8 kb) and pTMY625 (10.7 kb). The physical maps of these plasmids were as shown in FIG. 10, which also illustrates the overall process of the procedures described above.

Figure 13:
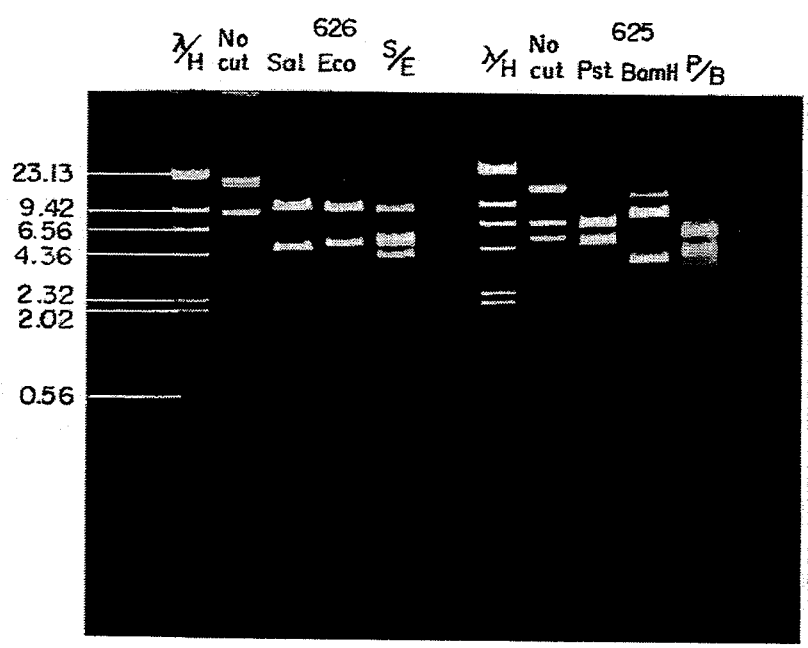
FIG. 13 is a picture showing the electrophoretic patterns of pTMY625, pTMY626 and various DNA fragments cut therefrom.

Electrophoretic patterns of pTMY625, pTMY626 and digests thereof with restriction enzymes are shown in FIG. 13. The symbols on top of the left side of the chart have the following meanings: λ/H, size marker of λ phage digested with HindIII; No cut, uncleaved pTMY626; Sal, pTMY626 SalI fragment; Eco, pTMY626 EcoRV fragment; and S/D, SalI-EcoRV fragment of pHMY626. The symbols on top of the right side of the chart have the following meanings: λ/H, size marker of λ phage digested with HindIII; No cut. uncleaved pTMY625; Pst, pTMY625 PstI fragment; BamHI, pTMY625 BamHI fragment; and P/B, PstI-BamHI fragment of pTMY625. The numerals on the left vertical axis of the chart represent the length of size markers in terms of kilobase pairs.

As shown in FIGS. 11 and 12, other shuttle vector plasmids pTMY631, pTMY632, pTMA641 and pTMA642 were constructed by the same procedures as those employed in constructing pTMY625 and pTMY626.

EXAMPLE 10

Transformation of E. coli and T. ferrooxidans with Shuttle Vector Plasmids

A. Transformation of E. coli

The shuttle vector plasmid pTMY625 or pTMY626 constructed in Example 9 was mixed with CaCl$_2$-treated E. coli DH5α so that is was incorporated into the latter. The plasmids were then cultured in a Luria broth at 37° C. for 1 hour. Each of the cultures was streaked onto a Luria agar plate containing 15 μg of HgCl$_2$ per ml and incubated at 37° C. overnight. On the next day, individual cell masses were collected with a toothpick and cultivated in Eppendorf tubes containing 1 ml of Luria broth loaded with 15 μg of HgCl$_2$ per ml. When they were in the stationary phase of growth, the cells were harvested by centrifugation at 6,000 rpm for 5 minutes and washed with 50 mM phosphate buffer (pH 7.4) once. The resulting cell pellets were resuspended in 200 μl of 50 mM phosphate buffer and disrupted supersonically (Branson Sonifier, setting 2, 20 seconds) on ice. The debris was removed by centrifugation at 15,000 rpm for 10 minutes and the supernatant was obtained as the crude extract.

Using this crude extract, assay was made for the mercury-dependent oxidation of NADPH by the same method as described in Example 1 under "C. Assay". Absorbance at 340 nm decreased as a result of incubation, Indicating the occurrence of NADPH oxidation.

B. Transformation of T. ferrooxidans Strain M4-6

Cells of T. ferrooxidans strain M4-6 in the logarithmic growth phase were harvested from 250 ml of 9K medium. The cell pellets were washed and used as host cells for transformation by electroporation which was conducted with a Gene Pulser TM of Bio-Rad.

In accordance with the operating manual for the Gene Pulser TM, the cells were suspended in an electroporation buffer. The cell suspension was mixed with 5 μg of shuttle vector plasmid pTMY625 or pTMY626. The mixture was put into a cuvette having an winter-electrode distance of 4 mm and left to stand at 0° C. for 30 minutes.

A 25-μF capacitor was discharged (6,250 V/cm) to effect electroporation. After the discharge, the cells were inoculated on 10 ml of 9K medium and incubated at 30° C. overnight, followed by cultivation for 7–10 days at 30° C. on silica gel plates containing 0.3 μg of HgCl₂ per ml. Colonies grown on the plates were transferred into 5 ml of 9K medium containing 0.3 μg of HgCl₂ per ml. The grown cells were treated as in Example 1-C to prepare extracts and the mercury volatilizing activity of the transformants was evaluated by examining mercury-dependent oxidation of NADPH.

The T. ferrooxidans transformants had mercury volatilizing activity.

C. Transformation of T. Ferrooxidans Strain K2-7

The recombinant vector plasmid pTMZ48 (Journal of Bacteriology, Oct. 1992, P. 6617–6623) was introduced to cells of T. ferrooxidans strain K2-7 by an electroporation as described in B. above. When colonies appeared on the Hg-containing silica gel plate, 56 colonies were respectively propagated in a liquid medium. The cells were harvested and the plasmids were isolated. The plasmid fraction was subjected to an electrophoresis on an agarose gel plate. The separated DNA was transferred to a membrane filter and Southern hybridization was performed with the mercury resistance gene from T. ferrooxidance (merC-merA) as a probe. As a result, at least 5 clones were shown to have the plasmid fraction which hybridized to the probe.

EXAMPLE 11

Sequencing of MerC Gene of T. ferrooxidans and Deduced Amine Acids

The region upstream of merA in the 4.6 kb SalI fragment was assumed to encode the 16 kDa protein. Thus the region was sequenced by the dideoxy nucleotide chain termination method using modified plasmid templates (Sanger's method). Genetic Information Processing Program purchased from SDC-GENETYX was employed in the analysis of the nucleotide and amino acid sequences.

The gene encoding the 16 kDa protein contained an open reading frame of 432 bp encoding 143 amino acids. The nucleotide sequence and the deduced amino acid sequence are shown in FIG. 14. The amino acid sequence showed a high homology (61%) with merC gene from plasmid R100 (FIG. 15). Therefore it was concluded that the gene encoding the 16 kDa protein was merC.

---

What is claimed is:

1. A 4.8 kb SalI-SalI DNA fragment isolated from genomic DNA of a *Thiobacillus ferrooxidans* mercury resistant strain, or a shorter fragment thereof having a size at least 2.3 kb and containing a 2.1 kb HindIII-HindIII segment, wherein said DNA fragment contains the 56 kDa mercuric reductase gene (merA) and the 16 kDa protein gene (merC), said DNA fragment hybridizes with the mercuric resistance gene of Pseudomonas transposen Tn501, and said DNA fragment provides mercury resistance with *Escherichia cell* cells when said cells are transformed with *E. coli* plasmid carrying said DNA fragment.

2. A DNA fragment according to claim 1, wherein said DNA fragment is derived from the genomic DNA of *T. ferrooxidans* strain E-15 (FERM BP-10217).

3. A DNA fragment according to claim 1, wherein the transformed *E. coli* cells have a minimum inhibitory concentration of HgCl$_2$ of at least 50 µg/ml of medium.

4. A DNA fragment according to claim 1, wherein said fragment is capable of providing mercury resistance with non-mercury resistant *T. ferrooxidans* cells when said cells are transformed with a plasmid containing said DNA fragment and a replication origin of *T. ferrooxidans*.

5. A DNA fragment according to claim 1, wherein the mercuric reductase encoded by merA in said DNA fragment has the following amine acid sequence:

```
          10         20         30         40         50
MTENAPTELAITGMTCDGCAAHVRKALEGVPGVREAQVSYPDATARVVLE 60         70         80         90        100
GEVPMQRLIKAVVASGYGVHPRSDGASSTNDGQELHIAVIGTGGAAMACA 110        120        130        140        150
LKAVERGARVTLIERSTIGGTCVNIGCVPSKIMIRAAHIAHLRRESPFDG 160        170        180        190        200
GIQAVAPTIQRTALLVQQQARVDELRHAKYEGILDGNPAITVLRGEARFK 210        220        230        240        250
DSRSVVVHLNDGGERVVMFDRCLVATGASPAVPPIPGLKDTPYWTSTEGL 260        270        280        290        300
VSESIPERLAVIGSSVVALELAQAFARLGSHVTILARGTLFLREDPAIGE 310        320        330        340        350
AITAAFRAEGIEVLEHTQASQVAYADGEFVLATGHGELRADKLLVATGRA 360        370        380        390        400
PNTRRLNLEAAGVAINAQGAIVIDQGMRTNSPNIYAAGDCTDQPQFVYVA 410        420        430        440        450
AAAGTRAAINMMGGSAALDLTAMPAVVFTDPQVATVGYSAEAHRDGIETD 460        470        480        490        500
SRMTLDNVPRALANFNTRGFIKLVAEVGSGSLIGVQVVAPEAGELIQTAA
```

510         520         530         540
LAIRNRMTVQELADQLFPYLTMVEGLKLAAQTFTRDVKQLSCCAG.

6. A DNA fragment according to claim 5, wherein merA gene of said DNA fragment has the following nucleotide sequence:

```
         10          20          30          40          50
ATGACCGAGAACGCGCCCACCGAACTCGCTATCACTGGCATGACCTGCGA 60          70          80          90         100
CGGTTGCGCCGCGCATGTGCGCAAAGCACTCGAAGGCGTGCCCGGCGTAC 110         120         130         140         150
GCGAGGCGCAGGTGTCCTACCCGGATGCCACGGCCCGGGTCGTGCTGGAG 160         170         180         190         200
GGCGAGGTGCCGATGCAGCGGCTAATCAAGGCGGTGGTTGCAAGTGGCTA 210         220         230         240         250
TGGTGTGCATCCACGGAGCGACGGTGCCTCCTCCACAAACGATGGACAGG 260         270         280         290         300
AGCTACACATCGCTGTGATCGGCACCGGCGGAGCGGCGATGGCGTGCGCA 310         320         330         340         350
TTGAAGGCTGTCGAGCGGGGCGCGCGCGTGACGCTGATCGAACGCAGCAC 360         370         380         390         400
CATCGGCGGCACCTGCGTGAACATCGGTTGCGTGCCGTCCAAGATCATGA 410         420         430         440         450
TCCGCGCCGCCCATATCGCCCACCTCCGCCGGGAAAGCCCATTCGATGGC 460         470         480         490         500
GGCATCCAGGCGGTCGCGCCGACCATCCAGCGCACAGCGCTGCTGGTCCA 510         520         530         540         550
ACAGCAGGCCCGTGTCGATGAACTGCGTCACGCCAAGTACGAAGGCATCC 560         570         580         590         600
TGGACGGCAACCCGGCCATCACCGTTCTGCGCGGTGAAGCGCGTTTCAAG 610         620         630         640         650
GACAGCCGGAGTGTTGTCGTCCATTTGAACGATGGTGGCGAGCGCGTCGT 660         670         680         690         700
AATGTTCGACCGCTGCCTGGTTGCCACGGGCGCCAGTCCGGCCGTGCCGC 710         720         730         740         750
CGATTCCCGGCTTGAAAGACACTCCTTATTGGACCTCCACCGAAGGGCTG 760         770         780         790         800
GTCAGCGAATCGATCCCCGAGCGTCTGGCCGTGATCGGCTCGTCGGTGGT 810         820         830         840         850
GGCGCTGGAACTGGCGCAAGCCTTCGCCCGGCTCGGCAGCCATGTGACGA 860         870         880         890         900
TCCTGGCGCGCGGCACCTTGTTCCTCCGGGAAGACCCGGCCATCGGTGAG 910         920         930         940         950
GCCATCACGGCGGCGTTTCGCGCCGAAGGCATCGAGGTGCTGGAGCACAC 960         970         980         990        1000
CCAGGCCAGCCAGGTCGCTTATGCGGATGGCGAATTTGTGCTAGCCACCG 1010        1020        1030        1040        1050
GGCACGGCGAACTGCGCGCCGATAAGCTGCTGGTCGCCACTGGTCGCGCA 1060        1070        1080        1090        1100
CCGAACACACGCCGCCTGAATCTGGAAGCGGCGGGCGTGGCCATCAATGC 1110        1120        1130        1140        1150
GCAAGGGGCCATCGTCATCGACCAGGGTATGCGCACGAACAGCCCGAACA 1160        1170        1180        1190        1200
TTTACGCCGCTGGCGACTGCACCGACCAGCCGCAATTCGTCTACGTGGCG
```

```
                    1210      1220      1230      1240      1250
          GCAGCGGCCGGCACCCGTGCGGCCATCAACATGATGGGCGGTAGTGCAGC 1260      1270      1280      1290      1300
          CCTGGACTTGACGGCGATGCCAGCCGTGGTGTTCACCGATCCGCAAGTGG 1310      1320      1330      1340      1350
          CGACTGTGGGTTACAGCGCGGAAGCGCATCGCGACGGCATCGAAACCGAC 1360      1370      1380      1390      1400
          AGCCGCATGACGCTCGACAACGTGCCGCGGGCGCTCGCCAATTTCAATAC 1410      1420      1430      1440      1450
          ACGCGGCTTCATCAAGCTGGTAGCCGAAGTGGGCAGTGGCTCGCTAATCG 1460      1470      1480      1490      1500
          GCGTGCAGGTGGTCGCCCCGGAAGCGGGCGAGCTGATCCAGACTGCCGCG 1510      1520      1530      1540      1550
          CTGGCGATTCGTAACCGGATGACGGTACAGGAACTGGCTGACCAGTTGTT 1560      1570      1580      1590      1600
          TCCCTACCTGACGATGGTCGAAGGGCTGAAGCTTGCTGCCCAGACCTTCA 1610      1620      1630
          CCAGGGATGTGAAGCAGTTGTCCTGCTGTGCGGGT.
```

7. A plasmid which comprises an *E. coli* plasmid together with a 4.8 kb SalI-SalI DNA fragment isolated from genomic DNA of a *Thiobacillus ferrooxidans* mercury resistant strain, or a shorter fragment thereof having a size at least 2.3 kb and containing a 2.1 kb HindIII-HindIII segment, wherein
said DNA fragment contains the 56 kDa mercuric reductase gene (merA) and the 16 kDa protein gene (merC),
said DNA fragment hybridizes with the mercuric resistance gene of Pseudomonas transposon Tn501, and
said DNA fragment provides mercury resistance with *Escherichia coli* cells when said cells are transformed with *E. coli* plasmid carrying said DNA fragment.

8. A plasmid according to claim 7, wherein said DNA fragment is derived from the genomic DNA of *T. ferrooxidans* strain E-15 (FERM BP-10217).

9. A plasmid according to claim 8, wherein the transformed *E. coli* cells have a minimum inhibitory concentration of $HgCl_2$ in a medium of at least 50 μg/ml.

10. A plasmid according to claim 7, wherein said fragment provides mercury resistance with non-mercury resistant *T. ferrooxidans* cells when said cells are transformed with a plasmid containing said DNA fragment and a replication origin of *T. ferrooxidans*.

11. A plasmid according to claim 7, wherein the mercuric reductase encoded by merA in said DNA fragment has the following amino acid sequence:

```
              10         20         30         40         50
     MTENAPTELAITGMTCDGCAAHVRKALEGVPGVREAQVSYPDATARVVLE 60         70         80         90        100
     GEVPMQRLIKAVVASGYGVHPRSDGASSTNDGQELHIAVIGTGGAAMACA 110        120        130        140        150
     LKAVERGARVTLIERSTIGGTCVNIGCVPSKIMIRAAHIAHLRRESPFDG 160        170        180        190        200
     GIQAVAPTIQRTALLVQQQARVDELRHAKYEGILDGNPAITVLRGEARFK 210        220        230        240        250
     DSRSVVVHLNDGGERVVMFDRCLVATGASPAVPPIPGLKDTPYWTSTEGL 260        270        280        290        300
     VSESIPERLAVIGSSVVALELAQAFARLGSHVTILARGTLFLREDPAIGE 310        320        330        340        350
     AITAAFRAEGIEVLEHTQASQVAYADGEFVLATGHGELRADKLLVATGRA 360        370        380        390        400
     PNTRRLNLEAAGVAINAQGAIVIDQGMRTNSPNIYAAGDCTDQPQFVYVA 410        420        430        440        450
     AAAGTRAAINMMGGSAALDLTAMPAVVFTDPQVATVGYSAEAHRDGIETD 460        470        480        490        500
     SRMTLDNVPRALANFNTRGFIKLVAEVGSGSLIGVQVVAPEAGELIQTAA 510        520        530        540
     LAIRNRMTVQELADQLFPYLTMVEGLKLAAQTFTRDVKQLSCCAG.
```

12. A plasmid according to claim 11, wherein merA gene of said DNA fragment has the following nucleotide sequence:

```
         10        20        30        40        50
ATGACCGAGAACGCGCCCACCGAACTCGCTATCACTGGCATGACCTGCGA 60        70        80        90       100
CGGTTGCGCCGCGCATGTGCGCAAAGCACTCGAAGGCGTGCCCGGCGTAC 110       120       130       140       150
GCGAGGCGCAGGTGTCCTACCCGGATGCCACGGCCCGGGTCGTGCTGGAG 160       170       180       190       200
GGCGAGGTGCCGATGCAGCGGCTAATCAAGGCGGTGGTTGCAAGTGGCTA 210       220       230       240       250
TGGTGTGCATCCACGGAGCGACGGTGCCTCCTCCACAAACGATGGACAGG 260       270       280       290       300
AGCTACACATCGCTGTGATCGGCACCGGCGGAGCGGCGATGGCGTGCGCA 310       320       330       340       350
TTGAAGGCTGTCGAGCGGGGCGCGCGCGTGACGCTGATCGAACGCAGCAC 360       370       380       390       400
CATCGGCGGCACCTGCGTGAACATCGGTTGCGTGCCGTCCAAGATCATGA 410       420       430       440       450
TCCGCGCCGCCCATATCGCCCACCTCCGCCGGGAAAGCCCATTCGATGGC 460       470       480       490       500
GGCATCCAGGCGGTCGCGCCGACCATCCAGCGCACAGCGCTGCTGGTCCA 510       520       530       540       550
ACAGCAGGCCCGTGTCGATGAACTGCGTCACGCCAAGTACGAAGGCATCC 560       570       580       590       600
TGGACGGCAACCCGGCCATCACCGTTCTGCGCGGTGAAGCGCGTTTCAAG 610       620       630       640       650
GACAGCCGGAGTGTTGTCGTCCATTTGAACGATGGTGGCGAGCGCGTCGT 660       670       680       690       700
AATGTTCGACCGCTGCCTGGTTGCCACGGGCGCCAGTCCGGCCGTGCCGC 710       720       730       740       750
CGATTCCCGGCTTGAAAGACACTCCTTATTGGACCTCCACCGAAGGGCTG 760       770       780       790       800
GTCAGCGAATCGATCCCCGAGCGTCTGGCCGTGATCGGCTCGTCGGTGGT 810       820       830       840       850
GGCGCTGGAACTGGCGCAAGCCTTCGCCCGGCTCGGCAGCCATGTGACGA 860       870       880       890       900
TCCTGGCGCGCGGCACCTTGTTCCTCCGGGAAGACCCGGCCATCGGTGAG 910       920       930       940       950
GCCATCACGGCGGCGTTTCGCGCCGAAGGCATCGAGGTGCTGGAGCACAC 960       970       980       990      1000
CCAGGCCAGCCAGGTCGCTTATGCGGATGGCGAATTTGTGCTAGCCACCG 1010      1020      1030      1040      1050
GGCACGGCGAACTGCGCGCCGATAAGCTGCTGGTCGCCACTGGTCGCGCA 1060      1070      1080      1090      1100
CCGAACACACGCCGCCTGAATCTGGAAGCGGCGGGCGTGGCCATCAATGC 1110      1120      1130      1140      1150
GCAAGGGGCCATCGTCATCGACCAGGGTATGCGCACGAACAGCCCGAACA 1160      1170      1180      1190      1200
TTTACGCCGCTGGCGACTGCACCGACCAGCCGCAATTCGTCTACGTGGCG 1210      1220      1230      1240      1250
GCAGCGGCCGGCACCCGTGCGGCCATCAACATGATGGGCGGTAGTGCAGC 1260      1270      1280      1290      1300
CCTGGACTTGACGGCGATGCCAGCCGTGGTGTTCACCGATCCGCAAGTGG
```

-continued

```
        1310      1320      1330      1340      1350
CGACTGTGGGTTACAGCGCGGAAGCGCATCGCGACGGCATCGAAACCGAC 1360      1370      1380      1390      1400
AGCCGCATGACGCTCGACAACGTGCCGCGGGCGCTCGCCAATTTCAATAC 1410      1420      1430      1440      1450
ACGCGGCTTCATCAAGCTGGTAGCCGAAGTGGGCAGTGGCTCGCTAATCG 1460      1470      1480      1490      1500
GCGTGCAGGTGGTCGCCCCGGAAGCGGGCGAGCTGATCCAGACTGCCGCG 1510      1520      1530      1540      1550
CTGGCGATTCGTAACCGGATGACGGTACAGGAACTGGCTGACCAGTTGTT 1560      1570      1580      1590      1600
TCCCTACCTGACGATGGTCGAAGGGCTGAAGCTTGCTGCCCAGACCTTCA 1610      1620      1630
CCAGGGATGTGAAGCAGTTGTCCTGCTGTGCGGGT.
```

13. A plasmid according to claim 12, wherein said *E. coli* plasmid is selected from pUC18 and pBR322.

14. A plasmid according to claim 13, wherein said plasmid further comprises a replication origin of *T. ferrooxidans* and said plasmid provides mercury resistance with mercury susceptible *T. ferrooxidans* cells when the cells are transformed with said plasmid.

15. A plasmid according to claim 14, wherein said replication origin of *T. ferrooxidans* is derived from plasmid pTSY91 (FERM BP-9157), plasmid pTSB121 (FERM BP-9156) or plasmid pTNA33 (FERM BP-10965).

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1635 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: T. ferrooxidans strain E-15

( i v ) IMMEDIATE SOURCE:
        ( C ) CLONE: plasmid pTM314

( i x ) FEATURE:
        ( D ) OTHER INFORMATION: expresses T. ferrooxidans merA ( x i ) SEQUENCE DESCRIPTION: SEQ ID NO:1:

```
ATG  ACC  GAG  AAC  GCG  CCC  ACC  GAA  CTC  GCT  ATC  ACT  GGC  ATG  ACC  TGC         48
Met  Thr  Glu  Asn  Ala  Pro  Thr  Glu  Leu  Ala  Ile  Thr  Gly  Met  Thr  Cys
 1             5                        10                       15

GAC  GGT  TGC  GCC  GCG  CAT  GTG  CGC  AAA  GCA  CTC  GAA  GGC  GTG  CCC  GGC         96
Asp  Gly  Cys  Ala  Ala  His  Val  Arg  Lys  Ala  Leu  Glu  Gly  Val  Pro  Gly
                    20                       25                       30

GTA  CGC  GAG  GCG  CAG  GTG  TCC  TAC  CCG  GAT  GCC  ACG  GCC  CGG  GTC  GTG        144
Val  Arg  Glu  Ala  Gln  Val  Ser  Tyr  Pro  Asp  Ala  Thr  Ala  Arg  Val  Val
          35                       40                       45

CTG  GAG  GGC  GAG  GTG  CCG  ATG  CAG  CGG  CTA  ATC  AAG  GCG  GTG  GTT  GCA        192
Leu  Glu  Gly  Glu  Val  Pro  Met  Gln  Arg  Leu  Ile  Lys  Ala  Val  Val  Ala
     50                       55                       60

AGT  GGC  TAT  GGT  GTG  CAT  CCA  CGG  AGC  GAC  GGT  GCC  TCC  TCC  ACA  AAC        240
Ser  Gly  Tyr  Gly  Val  His  Pro  Arg  Ser  Asp  Gly  Ala  Ser  Ser  Thr  Asn
 65                       70                       75                       80

GAT  GGA  CAG  GAG  CTA  CAC  ATC  GCT  GTG  ATC  GGC  ACC  GGC  GGA  GCG  GCG        288
```

|  |  |  |  |  |  |  |  |  |  |  |  |  |  |  |  |  |
|---|---|---|---|---|---|---|---|---|---|---|---|---|---|---|---|---|
| Asp | Gly | Gln | Glu | Leu | His | Ile | Ala | Val | Ile | Gly | Thr | Gly | Gly | Ala | Ala |  |
|  |  |  |  | 85 |  |  |  |  | 90 |  |  |  |  |  | 95 |  |
| ATG | GCG | TGC | GCA | TTG | AAG | GCT | GTC | GAG | CGG | GGC | GCG | CGC | GTG | ACG | CTG | 336 |
| Met | Ala | Cys | Ala | Leu | Lys | Ala | Val | Glu | Arg | Gly | Ala | Arg | Val | Thr | Leu |  |
|  |  |  |  | 100 |  |  |  |  | 105 |  |  |  |  | 110 |  |  |
| ATC | GAA | CGC | AGC | ACC | ATC | GGC | GGC | ACC | TGC | GTG | AAC | ATC | GGT | TGC | GTG | 384 |
| Ile | Glu | Arg | Ser | Thr | Ile | Gly | Gly | Thr | Cys | Val | Asn | Ile | Gly | Cys | Val |  |
|  |  |  | 115 |  |  |  |  | 120 |  |  |  |  | 125 |  |  |  |
| CCG | TCC | AAG | ATC | ATG | ATC | CGC | GCC | GCC | CAT | ATC | GCC | CAC | CTC | CGC | CGG | 432 |
| Pro | Ser | Lys | Ile | Met | Ile | Arg | Ala | Ala | His | Ile | Ala | His | Leu | Arg | Arg |  |
|  | 130 |  |  |  |  | 135 |  |  |  |  | 140 |  |  |  |  |  |
| GAA | AGC | CCA | TTC | GAT | GGC | GGC | ATC | CAG | GCG | GTC | GCG | CCG | ACC | ATC | CAG | 480 |
| Glu | Ser | Pro | Phe | Asp | Gly | Gly | Ile | Gln | Ala | Val | Ala | Pro | Thr | Ile | Gln |  |
| 145 |  |  |  |  | 150 |  |  |  |  | 155 |  |  |  |  | 160 |  |
| CGC | ACA | GCG | CTG | CTG | GTC | CAA | CAG | CAG | GCC | CGT | GTC | GAT | GAA | CTG | CGT | 528 |
| Arg | Thr | Ala | Leu | Leu | Val | Gln | Gln | Gln | Ala | Arg | Val | Asp | Glu | Leu | Arg |  |
|  |  |  |  | 165 |  |  |  |  | 170 |  |  |  |  | 175 |  |  |
| CAC | GCC | AAG | TAC | GAA | GGC | ATC | CTG | GAC | GGC | AAC | CCG | GCC | ATC | ACC | GTT | 576 |
| His | Ala | Lys | Tyr | Glu | Gly | Ile | Leu | Asp | Gly | Asn | Pro | Ala | Ile | Thr | Val |  |
|  |  |  | 180 |  |  |  |  | 185 |  |  |  |  | 190 |  |  |  |
| CTG | CGC | GGT | GAA | GCG | CGT | TTC | AAG | GAC | AGC | CGG | AGT | GTT | GTC | GTC | CAT | 624 |
| Leu | Arg | Gly | Glu | Ala | Arg | Phe | Lys | Asp | Ser | Arg | Ser | Val | Val | Val | His |  |
|  |  | 195 |  |  |  |  | 200 |  |  |  |  | 205 |  |  |  |  |
| TTG | AAC | GAT | GGT | GGC | GAG | CGC | GTC | GTA | ATG | TTC | GAC | CGC | TGC | CTG | GTT | 672 |
| Leu | Asn | Asp | Gly | Gly | Glu | Arg | Val | Val | Met | Phe | Asp | Arg | Cys | Leu | Val |  |
|  | 210 |  |  |  |  | 215 |  |  |  |  | 220 |  |  |  |  |  |
| GCC | ACG | GGC | GCC | AGT | CCG | GCC | GTG | CCG | CCG | ATT | CCC | GGC | TTG | AAA | GAC | 720 |
| Ala | Thr | Gly | Ala | Ser | Pro | Ala | Val | Pro | Pro | Ile | Pro | Gly | Leu | Lys | Asp |  |
| 225 |  |  |  |  | 230 |  |  |  |  | 235 |  |  |  |  | 240 |  |
| ACT | CCT | TAT | TGG | ACC | TCC | ACC | GAA | GGG | CTG | GTC | AGC | GAA | TCG | ATC | CCC | 768 |
| Thr | Pro | Tyr | Trp | Thr | Ser | Thr | Glu | Gly | Leu | Val | Ser | Glu | Ser | Ile | Pro |  |
|  |  |  |  | 245 |  |  |  |  | 250 |  |  |  |  | 255 |  |  |
| GAG | CGT | CTG | GCC | GTG | ATC | GGC | TCG | TCG | GTG | GTG | GCG | CTG | GAA | CTG | GCG | 816 |
| Glu | Arg | Leu | Ala | Val | Ile | Gly | Ser | Ser | Val | Val | Ala | Leu | Glu | Leu | Ala |  |
|  |  |  | 260 |  |  |  |  | 265 |  |  |  |  | 270 |  |  |  |
| CAA | GCC | TTC | GCC | CGG | CTC | GGC | AGC | CAT | GTG | ACG | ATC | CTG | GCG | CGC | GGC | 864 |
| Gln | Ala | Phe | Ala | Arg | Leu | Gly | Ser | His | Val | Thr | Ile | Leu | Ala | Arg | Gly |  |
|  |  | 275 |  |  |  |  | 280 |  |  |  |  | 285 |  |  |  |  |
| ACC | TTG | TTC | CTC | CGG | GAA | GAC | CCG | GCC | ATC | GGT | GAG | GCC | ATC | ACG | GCG | 912 |
| Thr | Leu | Phe | Leu | Arg | Glu | Asp | Pro | Ala | Ile | Gly | Glu | Ala | Ile | Thr | Ala |  |
|  | 290 |  |  |  |  | 295 |  |  |  |  | 300 |  |  |  |  |  |
| GCG | TTT | CGC | GCC | GAA | GGC | ATC | GAG | GTG | CTG | GAG | CAC | ACC | CAG | GCC | AGC | 960 |
| Ala | Phe | Arg | Ala | Glu | Gly | Ile | Glu | Val | Leu | Glu | His | Thr | Gln | Ala | Ser |  |
| 305 |  |  |  |  | 310 |  |  |  |  | 315 |  |  |  |  | 320 |  |
| CAG | GTC | GCT | TAT | GCG | GAT | GGC | GAA | TTT | GTG | CTA | GCC | ACC | GGG | CAC | GGC | 1008 |
| Gln | Val | Ala | Tyr | Ala | Asp | Gly | Glu | Phe | Val | Leu | Ala | Thr | Gly | His | Gly |  |
|  |  |  | 325 |  |  |  |  | 330 |  |  |  |  | 335 |  |  |  |
| GAA | CTG | CGC | GCC | GAT | AAG | CTG | CTG | GTC | GCC | ACT | GGT | CGC | GCA | CCG | AAC | 1056 |
| Glu | Leu | Arg | Ala | Asp | Lys | Leu | Leu | Val | Ala | Thr | Gly | Arg | Ala | Pro | Asn |  |
|  |  | 340 |  |  |  |  | 345 |  |  |  |  | 350 |  |  |  |  |
| ACA | CGC | CGC | CTG | AAT | CTG | GAA | GCG | GCG | GGC | GTG | GCC | ATC | AAT | GCG | CAA | 1104 |
| Thr | Arg | Arg | Leu | Asn | Leu | Glu | Ala | Ala | Gly | Val | Ala | Ile | Asn | Ala | Gln |  |
|  | 355 |  |  |  |  | 360 |  |  |  |  | 365 |  |  |  |  |  |
| GGG | GCC | ATC | GTC | ATC | GAC | CAG | GGT | ATG | CGC | ACG | AAC | AGC | CCG | AAC | ATT | 1152 |
| Gly | Ala | Ile | Val | Ile | Asp | Gln | Gly | Met | Arg | Thr | Asn | Ser | Pro | Asn | Ile |  |
| 370 |  |  |  |  | 375 |  |  |  |  | 380 |  |  |  |  |  |  |
| TAC | GCC | GCT | GGC | GAC | TGC | ACC | GAC | CAG | CCG | CAA | TTC | GTC | TAC | GTG | GCG | 1200 |
| Tyr | Ala | Ala | Gly | Asp | Cys | Thr | Asp | Gln | Pro | Gln | Phe | Val | Tyr | Val | Ala |  |
| 385 |  |  |  |  | 390 |  |  |  |  | 395 |  |  |  |  | 400 |  |
| GCA | GCG | GCC | GGC | ACC | CGT | GCG | GCC | ATC | AAC | ATG | ATG | GGC | GGT | AGT | GCA | 1248 |
| Ala | Ala | Ala | Gly | Thr | Arg | Ala | Ala | Ile | Asn | Met | Met | Gly | Gly | Ser | Ala |  |
|  |  |  | 405 |  |  |  |  | 410 |  |  |  |  | 415 |  |  |  |

```
GCC CTG GAC TTG ACG GCG ATG CCA GCC GTG GTG TTC ACC GAT CCG CAA      1296
Ala Leu Asp Leu Thr Ala Met Pro Ala Val Val Phe Thr Asp Pro Gln
        420                 425                 430

GTG GCG ACT GTG GGT TAC AGC GCG GAA GCG CAT CGC GAC GGC ATC GAA      1344
Val Ala Thr Val Gly Tyr Ser Ala Glu Ala His Arg Asp Gly Ile Glu
        435                 440                 445

ACC GAC AGC CGC ATG ACG CTC GAC AAC GTG CCG CGG GCG CTC GCC AAT      1392
Thr Asp Ser Arg Met Thr Leu Asp Asn Val Pro Arg Ala Leu Ala Asn
        450                 455                 460

TTC AAT ACA CGC GGC TTC ATC AAG CTG GTA GCC GAA GTG GGC AGT GGC      1440
Phe Asn Thr Arg Gly Phe Ile Lys Leu Val Ala Glu Val Gly Ser Gly
465                 470                 475                 480

TCG CTA ATC GGC GTG CAG GTG GTC GCC CCG GAA GCG GGC GAG CTG ATC      1488
Ser Leu Ile Gly Val Gln Val Val Ala Pro Glu Ala Gly Glu Leu Ile
                485                 490                 495

CAG ACT GCC GCG CTG GCG ATT CGT AAC CGG ATG ACG GTA CAG GAA CTG      1536
Gln Thr Ala Ala Leu Ala Ile Arg Asn Arg Met Thr Val Gln Glu Leu
            500                 505                 510

GCT GAC CAG TTG TTT CCC TAC CTG ACG ATG GTC GAA GGG CTG AAG CTT      1584
Ala Asp Gln Leu Phe Pro Tyr Leu Thr Met Val Glu Gly Leu Lys Leu
            515                 520                 525

GCT GCC CAG ACC TTC ACC AGG GAT GTG AAG CAG TTG TCC TGC TGT GCG      1632
Ala Ala Gln Thr Phe Thr Arg Asp Val Lys Gln Leu Ser Cys Cys Ala
530                 535                 540

GGT                                                                   1635
Gly
545
```

( 2 ) INFORMATION FOR SEQ ID NO:2:

( i ) SEQUENCE CHARACTERISTICS:
        ( A ) LENGTH: 545 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: T. ferrooxidans strain E-15

( i v ) IMMEDIATE SOURCE:
        ( C ) CLONE: plasmid pTM314

( x i ) SEQUENCE DESCRIPTION: SEQ ID NO:2:

```
Met Thr Glu Asn Ala Pro Thr Glu Leu Ala Ile Thr Gly Met Thr Cys
1               5                   10                  15

Asp Gly Cys Ala Ala His Val Arg Lys Ala Leu Glu Gly Val Pro Gly
                20                  25                  30

Val Arg Glu Ala Gln Val Ser Tyr Pro Asp Ala Thr Ala Arg Val Val
            35                  40                  45

Leu Glu Gly Glu Val Pro Met Gln Arg Leu Ile Lys Ala Val Val Ala
        50                  55                  60

Ser Gly Tyr Gly Val His Pro Arg Ser Asp Gly Ala Ser Ser Thr Asn
65                  70                  75                  80

Asp Gly Gln Glu Leu His Ile Ala Val Ile Gly Thr Gly Gly Ala Ala
                85                  90                  95

Met Ala Cys Ala Leu Lys Ala Val Glu Arg Gly Ala Arg Val Thr Leu
                100                 105                 110

Ile Glu Arg Ser Thr Ile Gly Gly Thr Cys Val Asn Ile Gly Cys Val
            115                 120                 125

Pro Ser Lys Ile Met Ile Arg Ala Ala His Ile Ala His Leu Arg Arg
```

```
               130                     135                     140
Glu Ser Pro Phe Asp Gly Gly Ile Gln Ala Val Ala Pro Thr Ile Gln
145                 150                 155                 160

Arg Thr Ala Leu Leu Val Gln Gln Gln Ala Arg Val Asp Glu Leu Arg
                165                 170                 175

His Ala Lys Tyr Glu Gly Ile Leu Asp Gly Asn Pro Ala Ile Thr Val
            180                 185                 190

Leu Arg Gly Glu Ala Arg Phe Lys Asp Ser Arg Ser Val Val Val His
        195                 200                 205

Leu Asn Asp Gly Gly Glu Arg Val Val Met Phe Asp Arg Cys Leu Val
    210                 215                 220

Ala Thr Gly Ala Ser Pro Ala Val Pro Pro Ile Pro Gly Leu Lys Asp
225                 230                 235                 240

Thr Pro Tyr Trp Thr Ser Thr Glu Gly Leu Val Ser Glu Ser Ile Pro
                245                 250                 255

Glu Arg Leu Ala Val Ile Gly Ser Ser Val Val Ala Leu Glu Leu Ala
                260                 265                 270

Gln Ala Phe Ala Arg Leu Gly Ser His Val Thr Ile Leu Ala Arg Gly
        275                 280                 285

Thr Leu Phe Leu Arg Glu Asp Pro Ala Ile Gly Glu Ala Ile Thr Ala
    290                 295                 300

Ala Phe Arg Ala Glu Gly Ile Glu Val Leu Glu His Thr Gln Ala Ser
305                 310                 315                 320

Gln Val Ala Tyr Ala Asp Gly Glu Phe Val Leu Ala Thr Gly His Gly
                325                 330                 335

Glu Leu Arg Ala Asp Lys Leu Leu Val Ala Thr Gly Arg Ala Pro Asn
                340                 345                 350

Thr Arg Arg Leu Asn Leu Glu Ala Ala Gly Val Ala Ile Asn Ala Gln
        355                 360                 365

Gly Ala Ile Val Ile Asp Gln Gly Met Arg Thr Asn Ser Pro Asn Ile
    370                 375                 380

Tyr Ala Ala Gly Asp Cys Thr Asp Gln Pro Gln Phe Val Tyr Val Ala
385                 390                 395                 400

Ala Ala Ala Gly Thr Arg Ala Ala Ile Asn Met Met Gly Gly Ser Ala
                405                 410                 415

Ala Leu Asp Leu Thr Ala Met Pro Ala Val Val Phe Thr Asp Pro Gln
                420                 425                 430

Val Ala Thr Val Gly Tyr Ser Ala Glu Ala His Arg Asp Gly Ile Glu
        435                 440                 445

Thr Asp Ser Arg Met Thr Leu Asp Asn Val Pro Arg Ala Leu Ala Asn
    450                 455                 460

Phe Asn Thr Arg Gly Phe Ile Lys Leu Val Ala Glu Val Gly Ser Gly
465                 470                 475                 480

Ser Leu Ile Gly Val Gln Val Val Ala Pro Glu Ala Gly Glu Leu Ile
                485                 490                 495

Gln Thr Ala Ala Leu Ala Ile Arg Asn Arg Met Thr Val Gln Glu Leu
            500                 505                 510

Ala Asp Gln Leu Phe Pro Tyr Leu Thr Met Val Glu Gly Leu Lys Leu
        515                 520                 525

Ala Ala Gln Thr Phe Thr Arg Asp Val Lys Gln Leu Ser Cys Cys Ala
    530                 535                 540

Gly
545
```

( 2 ) INFORMATION FOR SEQ ID NO:3:

( i ) SEQUENCE CHARACTERISTICS:
        ( A ) LENGTH: 1635 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: T. ferrooxidans strain E-15

( v i i ) IMMEDIATE SOURCE:
        ( C ) CLONE: plasmid pTM314

( i x ) FEATURE:
        ( D ) OTHER INFORMATION: expresses T. ferrooxidans merA ( x i ) SEQUENCE DESCRIPTION: SEQ ID NO:3:

```
ATGACCGAGA ACGCGCCCAC CGAACTCGCT ATCACTGGCA TGACCTGCGA CGGTTGCGCC        60
GCGCATGTGC GCAAAGCACT CGAAGGCGTG CCCGGCGTAC GCGAGGCGCA GGTGTCCTAC       120
CCGGATGCCA CGGCCCGGGT CGTGCTGGAG GGCGAGGTGC CGATGCAGCG GCTAATCAAG       180
GCGGTGGTTG CAAGTGGCTA TGGTGTGCAT CCACGGAGCG ACGGTGCCTC CTCCACAAAC       240
GATGGACAGG AGCTACACAT CGCTGTGATC GGCACCGGCG GAGCGGCGAT GGCGTGCGCA       300
TTGAAGGCTG TCGAGCGGGG CGCGCGCGTG ACGCTGATCG AACGCAGCAC CATCGGCGGC       360
ACCTGCGTGA ACATCGGTTG CGTGCCGTCC AAGATCATGA TCCGCGCCGC CCATATCGCC       420
CACCTCCGCC GGGAAAGCCC ATTCGATGGC GGCATCCAGG CGGTCGCGCC GACCATCCAG       480
CGCACAGCGC TGCTGGTCCA ACAGCAGGCC CGTGTCGATG AACTGCGTCA CGCCAAGTAC       540
GAAGGCATCC TGGACGGCAA CCCGGCCATC ACCGTTCTGC GCGGTGAAGC GCGTTTCAAG       600
GACAGCCGGA GTGTTGTCGT CCATTTGAAC GATGGTGGCG AGCGCGTCGT AATGTTCGAC       660
CGCTGCCTGG TTGCCACGGG CGCCAGTCCG GCCGTGCCGC CGATTCCCGG CTTGAAAGAC       720
ACTCCTTATT GGACCTCCAC CGAAGGGCTG GTCAGCGAAT CGATCCCCGA GCGTCTGGCC       780
GTGATCGGCT CGTCGGTGGT GGCGCTGGAA CTGGCGCAAG CCTTCGCCCG GCTCGGCAGC       840
CATGTGACGA TCCTGGCGCG CGGCACCTTG TTCCTCCGGG AAGACCCGGC CATCGGTGAG       900
GCCATCACGG CGGCGTTTCG CGCCGAAGGC ATCGAGGTGC TGGAGCACAC CAGGCCAGC       960
CAGGTCGCTT ATGCGGATGG CGAATTTGTG CTAGCCACCG GCACGGCGA ACTGCGCGCC      1020
GATAAGCTGC TGGTCGCCAC TGGTCGCGCA CCGAACACAC GCCGCCTGAA TCTGGAAGCG      1080
GCGGGCGTGG CCATCAATGC GCAAGGGGCC ATCGTCATCG ACCAGGGTAT GCGCACGAAC      1140
AGCCCGAACA TTTACGCCGC TGGCGACTGC ACCGACCAGC CGCAATTCGT CTACGTGGCG      1200
GCAGCGGCCG GCACCCGTGC GGCCATCAAC ATGATGGGCG GTAGTGCAGC CCTGGACTTG      1260
ACGGCGATGC CAGCCGTGGT GTTCACCGAT CCGCAAGTGG CGACTGTGGG TTACAGCGCG      1320
GAAGCGCATC GCGACGGCAT CGAAACCGAC AGCCGCATGA CGCTCGACAA CGTGCCGCGG      1380
GCGCTCGCCA ATTTCAATAC ACGCGGCTTC ATCAAGCTGG TAGCCGAAGT GGGCAGTGGC      1440
TCGCTAATCG GCGTGCAGGT GGTCGCCCCG GAAGCGGGCG AGCTGATCCA GACTGCCGCG      1500
CTGGCGATTC GTAACCGGAT GACGGTACAG GAACTGGCTG ACCAGTTGTT TCCCTACCTG      1560
ACGATGGTCG AAGGGCTGAA GCTTGCTGCC CAGACCTTCA CCAGGGATGT GAAGCAGTTG      1620
TCCTGCTGTG CGGGT                                                       1635
```

( 2 ) INFORMATION FOR SEQ ID NO:4:

( i ) SEQUENCE CHARACTERISTICS:
        ( A ) LENGTH: 568 base pairs (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: T. ferrooxidans strain E-15

(vii) IMMEDIATE SOURCE:
(C) CLONE: plasmid pTM314

(ix) FEATURE:
(A) OTHER INFORMATION: expresses T. ferrooxidans merC (xi) SEQUENCE DESCRIPTION: SEQ ID NO:4:

| | | | | | |
|---|---|---|---|---|---|
| GTACGGCAGT | AAGTTGGGCC | TACCCAACCC | CTATAATAAG | CTTATATCGT | GATGACATAG | 60 |

| | | | | | | | | | | | | | |
|---|---|---|---|---|---|---|---|---|---|---|---|---|---|
| CGTGATGACC | AGGAGGATCT | GTCC | ATG | TCA | GCC | ATA | ACC | CGC | ATC | ATC | GAC | | 111 |
| | | | Met | Ser | Ala | Ile | Thr | Arg | Ile | Ile | Asp | | |
| | | | 1 | | | | 5 | | | | | | |

| AAA | ATT | GGC | ATA | GTC | GGT | ACC | ATC | GTC | GGT | AGT | TTC | AGT | TGC | GCC | ATG | 159 |
|---|---|---|---|---|---|---|---|---|---|---|---|---|---|---|---|---|
| Lys | Ile | Gly | Ile | Val | Gly | Thr | Ile | Val | Gly | Ser | Phe | Ser | Cys | Ala | Met | |
| 10 | | | | 15 | | | | | 20 | | | | | | 25 | |

| TGT | TTC | CCC | GCA | GCA | GCG | AGC | CTC | GGC | GCT | GCA | ATC | GGA | TTG | GGC | TTT | 207 |
|---|---|---|---|---|---|---|---|---|---|---|---|---|---|---|---|---|
| Cys | Phe | Pro | Ala | Ala | Ala | Ser | Leu | Gly | Ala | Ala | Ile | Gly | Leu | Gly | Phe | |
| | | | | 30 | | | | | 35 | | | | | 40 | | |

| CTC | AGC | CAG | TGG | GAA | GGC | CTG | TTC | GTG | CAG | TGG | CTG | ATT | CCG | ATT | TTC | 255 |
|---|---|---|---|---|---|---|---|---|---|---|---|---|---|---|---|---|
| Leu | Ser | Gln | Trp | Glu | Gly | Leu | Phe | Val | Gln | Trp | Leu | Ile | Pro | Ile | Phe | |
| | | | 45 | | | | | 50 | | | | | 55 | | | |

| GCC | AGC | GTG | GCA | TTA | TTG | GCG | ACC | TTG | GCG | GGC | TGG | TTC | TCG | CAC | CGC | 303 |
|---|---|---|---|---|---|---|---|---|---|---|---|---|---|---|---|---|
| Ala | Ser | Val | Ala | Leu | Leu | Ala | Thr | Leu | Ala | Gly | Trp | Phe | Ser | His | Arg | |
| | | 60 | | | | 65 | | | | | 70 | | | | | |

| CAA | TGG | CAA | CGC | ACG | CTG | CTG | GGC | TCG | ATC | GGT | CCG | GTG | CTA | GCG | CTT | 351 |
|---|---|---|---|---|---|---|---|---|---|---|---|---|---|---|---|---|
| Gln | Trp | Gln | Arg | Thr | Leu | Leu | Gly | Ser | Ile | Gly | Pro | Val | Leu | Ala | Leu | |
| | 75 | | | | | 80 | | | | | 85 | | | | | |

| GTC | GGG | GTG | TTT | GGG | TTA | ACG | CAT | CAC | TTT | CTG | GAC | AAG | GAC | CTG | GCG | 399 |
|---|---|---|---|---|---|---|---|---|---|---|---|---|---|---|---|---|
| Val | Gly | Val | Phe | Gly | Leu | Thr | His | His | Phe | Leu | Asp | Lys | Asp | Leu | Ala | |
| 90 | | | | 95 | | | | | 100 | | | | | 105 | | |

| CGC | GTA | ATT | TTT | TAT | ACC | GGA | TTG | GTG | GTG | ATG | TTC | CTT | GTC | TCC | ATC | 447 |
|---|---|---|---|---|---|---|---|---|---|---|---|---|---|---|---|---|
| Arg | Val | Ile | Phe | Tyr | Thr | Gly | Leu | Val | Val | Met | Phe | Leu | Val | Ser | Ile | |
| | | | 110 | | | | | 115 | | | | | 120 | | | |

| TGG | GAC | ATG | GTC | AAT | CCG | GCG | AAC | CGC | TGC | GCG | ACC | GAC | GGC | TGC | GAA | 495 |
|---|---|---|---|---|---|---|---|---|---|---|---|---|---|---|---|---|
| Trp | Asp | Met | Val | Asn | Pro | Ala | Asn | Arg | Cys | Ala | Thr | Asp | Gly | Cys | Glu | |
| | | 125 | | | | | 130 | | | | | 135 | | | | |

| ACG | CCC | GCC | CCG | CGT | AGC | TGA | GCACATAGAC | ACTTTGGAGG | ATATT | ATG | ACC | 547 |
|---|---|---|---|---|---|---|---|---|---|---|---|---|
| Thr | Pro | Ala | Pro | Arg | Ser | STP | | | | Met | Thr | |
| | | 140 | | | | | | | | | 145 | |

| GAG | AAC | GCG | CCC | ACC | GAA | CTC | 568 |
|---|---|---|---|---|---|---|---|
| Glu | Asn | Ala | Pro | Thr | Glu | Leu | |
| | | | | | | 150 | |

(2) INFORMATION FOR SEQ ID NO:5:

(i) SEQUENCE CHARACTERISTICS:
(A) LENGTH: 140 amino acids
(B) TYPE: amino acid
(C) STRANDEDNESS: single
(D) TOPOLOGY: linear (ii) MOLECULE TYPE: peptide (vii) IMMEDIATE SOURCE:
(C) CLONE: plasmid R100

(xi) SEQUENCE DESCRIPTION: SEQ ID NO:5:

| Met | Gly | Leu | Met | Thr | Arg | Ile | Ala | Asp | Lys | Thr | Gly | Ala | Leu | Gly |
|---|---|---|---|---|---|---|---|---|---|---|---|---|---|---|
| | | | | 5 | | | | | 10 | | | | | 15 |

| | | | | | | | | | | | | |
|---|---|---|---|---|---|---|---|---|---|---|---|---|
|Ser|Val|Val|Ser|Ala 20|Met|Gly|Cys|Ala 25|Cys|Phe|Pro|Ala|Leu 30|
|Ala|Ser|Phe|Gly|Ala 35|Ala|Ile|Gly|Leu|Gly 40|Phe|Leu|Ser|Gln|Tyr 45|
|Glu|Gly|Leu|Phe|Ile 50|Ser|Arg|Leu|Leu|Pro 55|Leu|Phe|Ala|Ala|Leu 60|
|Ala|Phe|Leu|Ala|Asn 65|Ala|Leu|Gly|Trp|Phe 70|Ser|His|Arg|Gln|Trp 75|
|Leu|Arg|Ser|Leu|Leu 80|Gly|Met|Ile|Gly|Pro 85|Ala|Ile|Val|Phe|Ala 90|
|Ala|Thr|Val|Trp|Leu 95|Leu|Gly|Asn|Trp|Trp 100|Thr|Ala|Asn|Leu|Met 105|
|Tyr|Val|Gly|Leu|Ala 110|Leu|Met|Ile|Gly|Val 115|Ser|Ile|Trp|Asp|Phe 120|
|Val|Ser|Pro|Ala|His 125|Arg|Arg|Cys|Gly|Pro 130|Asp|Gly|Cys|Glu|Leu 135|
|Pro|Ala|Lys|Arg|Leu 140|